US007517667B2

(12) United States Patent
Murphy et al.

(10) Patent No.: US 7,517,667 B2
(45) Date of Patent: Apr. 14, 2009

(54) METHODS FOR PROMOTING, INHIBITING AND DETECTING TOXIN ENTRY INTO CELLS

(75) Inventors: John R. Murphy, Boston, MA (US); Ryan Ratts, Boston, MA (US)

(73) Assignee: Boston Medical Center Corporation, Boston, MA (US)

( * ) Notice: Subject to any disclaimer, the term of this patent is extended or adjusted under 35 U.S.C. 154(b) by 163 days.

(21) Appl. No.: 11/214,997

(22) Filed: Aug. 30, 2005

(65) Prior Publication Data

US 2007/0238670 A1 Oct. 11, 2007

Related U.S. Application Data

(63) Continuation-in-part of application No. PCT/US2004/009829, filed on Mar. 31, 2004.

(60) Provisional application No. 60/459,185, filed on Mar. 31, 2003.

(51) Int. Cl.

| | |
|---|---|
| *C12P 1/00* | (2006.01) |
| *C12P 21/04* | (2006.01) |
| *C12Q 1/02* | (2006.01) |
| *A61K 38/00* | (2006.01) |

(52) U.S. Cl. .......................... 435/41; 435/29; 435/71.3; 514/2

(58) Field of Classification Search ....................... None
See application file for complete search history.

(56) References Cited

U.S. PATENT DOCUMENTS 5,843,462 A 12/1998 Conti-Fine

FOREIGN PATENT DOCUMENTS

WO WO 2005/014798 2/2005

OTHER PUBLICATIONS

Abrami et al., "Membrane Insertion of Anthrax Protective Antigen and Cytoplasmic Delivery of Lethal Factor Occur at Different Stages of the Endocytic Pathway," *J. Cell Biol.* 166:645-651, 2004.

Ariansen et al., "Membrane Translocation of Diphtheria Toxin A-Fragment: Role of Carboxy-Terminal Region," *Biochem.* 32:83-90, 1993.

Arora et al., "Fusions of Anthrax Toxin Lethal Factor with Shiga Toxin and Diphtheria Toxin Enzymatic Domains are Toxic to Mammalian Cells," *Infect. Immun.* 62:4955-4961, 1994.

Arora et al., "Residues 1-254 of Anthrax Toxin Lethal Factor are Sufficient to Cause Cellular Uptake of Fused Polypeptides," *J. Biol. Chem.* 268: 3334-3341, 1993.

Bacha et al., "Interleukin 2 Receptor-Targeted Cytotoxicity. Interleukin 2 Receptor-Mediated Action of a Diphtheria Toxin-Related Interleukin 2 Fusion Protein," *J. Exp. Med.* 167:612-622, 1988.

Bennett et al., "Domain Swapping: Entangling Alliances Between Proteins," *Proc. Natl. Acad. Sci. USA* 91:3127-3131, 1994.

Bharti et al., "Identification of a Nucleolin Binding Site in Human Topoisomerase I," *J. Biol. Chem.* 271:1993-1997, 1996.

Binz et al., "Arg362 and Tyr365 of the Botulinum Neurotoxin Type A Light Chain are Involved in Transition State Stabilization," *Biochem.* 41:1717-1723, 2002.

Boquet et al., "Binding of Triton X-100 to Diphtheria Toxin, Crossreacting Material 45, and their Fragments," *Proc.Natl. Acad. Sci. USA* 73:4449-4453, 1976.

Chadwick et al., "Cytotoxicity of a Recombinant Diphtheria Toxin-Granulocyte Colony-Stimulating Factor Fusion Protein on Human Leukemic Blast Cells," *Leuk. Lymphoma* 11:249-262, 1993.

Chung et al., "The Mechanism of ADP-Ribosylation of Elongation Factor 2 Catalyzed by Fragment A from Diptheria Toxin," *Biochem. Biophys. Acta.* 483:248-257, 1977.

Donovan et al., "Diphtheria Toxin Forms Transmembrane Channels in Planar Lipid Bilayers," *Proc. Natl. Acad. Sci.*, USA 78:172-176, 1981.

Duden et al., "β-COP, A 110 kd Protein Associated with Non-Clathrin-Coated Vesicles and the Golgi Complex, Shows Homology to β-Adaptin," *Cell* 64:649-665, 1991.

Duprez et al., "Receptor-Mediated Endocytosis of Interleukin 2 in a Human Tumor T Cell Line. Degradation of Interleukin 2 and Evidence for the Absence of Recycling of Interleukin Receptors," *J. Biol. Chem.* 261:15450-15454, 1986.

Haug et al., "The Host Cell Chaperone Hsp90 is Necessary for Cytotoxic Action of the Binary Iota-Like Toxins," *Infect. Immun.* 72:3066-3068, 2004.

Hu et al., "The Effects of Helix Breaking Mutations in the Diphtheria Toxin Transmembrane Domain Helix Layers of the Fusion Toxin $DAB_{389}$IL-2," *Protein Eng.* 11:811-817, 1998.

Jackson et al., "The KDEL Retrieval System is Exploited by *Pseudomonas* Exotoxin A, but not by Shiga-Like Toxin-1, During Retrograde Transport from the Golgi Complex to the Endoplasmic Reticulum," *J. Cell Sci.* 112:467-475, 1999.

Jean et al., "Diphtheria Toxin Receptor-Binding Domain Substitution with Interleukin 6: Genetic Construction and Interleukin 6 Receptor-Specific Action of a Diphtheria Toxin-Related Interleukin 6 Fusion Protein," *Protein Eng.* 4:989-994, 1991.

(Continued)

*Primary Examiner*—Lisa J Hobbs
(74) *Attorney, Agent, or Firm*—Clark & Elbing LLP

(57) ABSTRACT

In vitro delivery of the diphtheria toxin (DT) catalytic (C) domain from the lumen of purified early endosomes to the external milieu requires the addition of both ATP and a cytosolic translocation factor (CTF) complex. The results presented here demonstrate that β-COP plays an essential role in the cytosolic release of the C-domain and is mediated by a consensus peptide sequence found on several bacterial toxins and in HIV-1 reverse transcriptase. The invention features methods for inhibiting cell death that include the administration of compounds based on this consensus sequence that inhibit the translocation of the catalytic domain of toxins or transcription factors. Also featured are methods for identifying compounds that inhibit cell death, and methods for identifying compounds that promote cell death by blocking or accelerating, respectively, the rate of toxin/factor endosomal translocation.

22 Claims, 4 Drawing Sheets

OTHER PUBLICATIONS

Kagan et al., "Diphtheria Toxin Fragment Forms Large Pores in Phospholipid Bilayer Membranes," *Proc. Natl. Acad. Sci.*, USA 78:4950-4954, 1981.

Kelley et al., "Interleukin 2-Diphtheria Toxin Fusion Protein Can Abolish Cell-Mediated Immunity In Vivo," *Proc. Natl. Acad. Sci. USA*85:3980-3984, 1988.

Kiyokawa et al., "Cytotoxicity of Interleukin 2-Toxin Toward Lymphocytes from Patients with Adult T-Cell Leukemia," *Cancer Res.* 49:4042-4046, 1989.

Kiyokawa et al., "Protein Engineering of DAB-IL-2 Fusion Toxins to Increase Biologic Potency," *Ann. NY Acad. Sci.* 636:331-339, 1991.

Kiyokawa et al., "Protein Engineering of Diphtheria-Toxin-Related Interleukin-2 Fusion Toxins to Increase Cytotoxic Potency for High-Affinity IL-2-Receptor-Bearing Target Cells," *Protein Eng.* 4:463-468, 1991.

Kochi et al., "DNA Fragmentation and Cytolysis in U937 Cells Treated with Diphtheria Toxin or Other Inhibitors of Protein Synthesis," *Exp. Cell. Res.* 208:296-302, 1993.

Lacy et al. "Mapping the Anthrax Protective Antigen Binding Site on the Lethal and Edema Factors," *J. Biol. Chem.* 277:3006-3010, 2002.

Lemichez et al., "Membrane Translocation of Diphtheria Toxin Fragment A Exploits Early to Late Endosome Trafficking Machinery," *Mol. Microbiol.* 23:445-457, 1997.

Liger et al., "The Diphtheria Toxin Transmembrane Domain as a pH Sensitive Membrane Anchor for Human Interleukin-2 and Murine Interleukin-3," *Protein Eng.* 11:1111-1120, 1998.

Lord et al., "Toxin Entry: Retrograde Transport Through the Secretory Pathway," *J. Cell Biol.* 140:733-736, 1998.

Love et al., "*Corynebacterium diphtheriae*: Iron-Mediated Activation of DtxR and Regulation of Diphtheria Toxin Expression," *Gram-Positive Pathogens*, 573-582, 2000.

McMahon et al., "COP and Clathrin-Coated Vesicle Budding: Different Pathways, Common Approaches," *Curr. Opin. Cell Biol.* 16:379-391, 2004.

Mitamura et al., "The 27-kD Diphtheria Toxin Receptor-Associated Protein (DRAP27) From Vero Cells is the Monkey Homologue of Human CD9 Antigen: Expression of DRAP27 Elevates the Number of Diphtheria Toxin Receptors on Toxin-Sensitive Cells," *J. Cell Biol.* 118:1389-1399, 1992.

Moya et al., "Inhibition of Coated Pit Formation in $Hep_2$ Cells Blocks the Cytotoxicity of Diphtheria toxin but not that of Ricin Toxin," *J. Cell. Biol.* 101:548-559, 1985.

Murphy et al., "Cell Receptor Specific Targeted Toxins: Genetic Construction and Characterization of an Interleukin 2 Diphtheria toxin-Related Fusion Protein," *J. Recept. Res.* 8:467-480, 1988.

Murphy, "Diphtheria-Related Peptide Hormone Gene Fusions: A Molecular Genetic Approach to Chimeric Toxin Development," *Cancer Treat. Res.* 37:123-140, 1988.

Murphy et al., "Genetic Assembly and Selective Toxicity of Diphtheria-Toxin-Related Polypeptide Hormone Fusion Proteins," *Biochem. Soc. Symp.* 53:9-23, 1987.

Murphy et al., "Interleukin 2 Toxin: A Step Toward Selective Immunomodulation," *Am. J. Kidney Dis.* 11:159-162, 1988.

Murphy et al., "Protein Engineering of Diphtheria Toxin. Development of Receptor-Specific Cytotoxic Agents for the Treatment of Human Disease," *Targeted Diagn. Ther.* 7:365-382, 1992.

Murphy et al., "Targeting Diphtheria Toxin to Growth Factor Receptors," *Semin. Cancer Biol.* 6:259-267, 1995.

O'Keefe et al., "pH-Dependent Insertion of Proteins into Membranes: B-Chain Mutation of Diphtheria Toxin that Inhibits Membrane Translocation Glu-349→Lys," *Proc. Natl. Acad. Sci. USA* 89:6202-6206, 1992.

Oh et al., "Translocation of the Catalytic Domain of Diphtheria Toxin Across Planar Phospholipid Bilayers by its Own T Domain," *Proc. Natl. Acad. Sci. USA* 96:8467-8470, 1999.

Perentesis et al., "Expression of Diphtheria Toxin Fragment A and Hormone-Toxin Fusion Proteins in Toxin-Resistant Yeast Mutants," *Proc. Natl. Acad. Sci. USA* 85:8386-8390, 1988.

Ratts et al., "Diphtheria Toxin-Structure, Function, and its Clinical Applications," *Chimeric Toxins* 14-36, 2002.

Ratts et al., "The Cytosolic Entry of Diphtheria Toxin Catalytic Domain Requires a Host Cell Cytosolic Translocation Factor Complex," *J. Cell. Biol.* 160:1139-1150, 2003.

Rebbe et al., "Nucleotide Sequence and Regulation of a Human 90-kDa Heat Shock Protein Gene," *J. Biol. Chem.* 264:15006-15011, 1989.

Ren et al., "Interaction of Diphtheria Toxin T Domain with Molten Globule-Like Proteins and its Implications for Translocation," *Science* 284:955-957, 1999.

Sandvig et al., "Pathways Followed by Protein Toxins Into Cells," *Int. J. Med. Microbiol.* 293:483-490, 2004.

Tsuneoka et al., "Evidence for Involvement of Furin in Cleavage and Activation of Diphtheria Toxin," *J. Biol. Chem.* 268:26461-26465, 1993.

Uchida, "Diphtheria Toxin and Related Proteins. I. Isolation and Properties of Mutant Proteins Serologically Related to Diphtheria Toxin," *J. Biol. Chem.* 248:3838-3844, 1973.

VanderSpek et al., "An Intact Transmembrane Helix 9 is Essential for the Efficient Delivery of the Diphtheria Toxin Catalytic Domain to the Cytosol of Target Cells," *J. Biol. Chem.* 269:21455-21459, 1994.

VanderSpek et al., "$DAB_{389}$ Interleukin-2 Receptor Binding Domain Mutations. Cytotoxic Probes for Studies of Ligand-Receptor Interactions," *J. Biol. Chem.* 271:12145-12149, 1996.

VanderSpek et al., "Epitope Tagging of $DAB_{389}$IL-2: New Insights into C-Domain Delivery to the Cytosol of Target Cells," *Leukemia* 8:S144-S148, 1994.

VanderSpek et al., "Genetic Construction and Characterization of the Diphtheria Toxin-Related Interleukin 15 Fusion Protein $DAB_{389}$ sIL-15," *Protein Eng.* 8:1317-1321, 1995.

VanderSpek et al., "Maintenance of the Hydrophobic Face of the Diphtheria Toxin Amphipathic Transmembrane Helix 1 is Essential for the Efficient Delivery of the Catalytic Domain to the Cytosol of Target Cells," *Protein Eng.* 7:985-989, 1994.

VanderSpek et al., "Structure/Function Analysis of the Transmembrane Domain of $DAB_{389}$-Interleukin-2, an Interleukin-2 Receptor-Targeted Fusion Toxin. The Amphipathic Helical Region of the Transmembrane Domain is Essential for the Efficient Delivery of the Catalytic Domain to the Cytosol of Target Cells," *J. Biol. Chem.* 268:12077-12082, 1993.

Walz et al., "Sequential Effects of Interleukin 2-Diphtheria Toxin Fusion Protein on T-Cell Activation," *Proc. Natl. Acad. Sci. USA* 86:9485-9488, 1989.

Waters et al., "Interleukin 2 Receptor-Targeted Cytotoxicity. Receptor Binding Requirements for Entry of a Diphtheria Toxin-Related Interleukin 2 Fusion Protein into Cells," *Eur. J. Immunol.* 20:785-791, 1990.

Wesche et al., "Characterization of Membrane Translocation by Anthrax Protective Antigen," *Biochemistry* 37:15737-15746, 1998.

Williams et al., "Cellular Processing of the Interleukin-2 Fusion Toxin $DAB_{486}$-IL-2 and Efficient Delivery of Diphtheria Fragment A to the Cytosol of Target Cells Requires $Arg^{194}$," *J. Biol. Chem.* 265:20673-20677, 1990.

Williams et al., "Structure/Function Analysis of Interleukin-2-Toxin ($DAB_{486}$-IL-2). Fragment B Sequences Required for the Delivery of Fragment A to the Cytosol of Target Cells," *J. Biol. Chem.* 265:11885-11889, 1990.

Zhang et al., "Evidence that Translocation of Anthrax Toxin's Lethal Factor is Initiated by Entry of its N Terminus into the Protective Antigen Channel," *Proc. Natl. Acad. Sci. USA* 101:16756-16761, 2004.

(A)

(B)

$DAB_{389}$IL-2 (210-229) Peptide Sequence
MRDKTKTKIESLKEHGPIKNK

METHODS FOR PROMOTING, INHIBITING AND DETECTING TOXIN ENTRY INTO CELLS

CROSS-REFERENCE TO RELATED APPLICATIONS

This application is a continuation-in-part of International Application No. PCT/US2004/09829, filed Mar. 31, 2004, which claims priority from U.S. Provisional Application No. 60/459,185, filed Mar. 31, 2003, each of which is hereby incorporated by reference in their entirety.

STATEMENT AS TO FEDERALLY FUNDED RESEARCH

This invention was made with Government Support under Grant CA60934 from the National Cancer Institute, as well as grants from the National Institute of Allergy and Infectious Disease (Grant Nos. AI021628 and AI057159). The U.S. Government has certain rights in the invention.

BACKGROUND OF THE INVENTION

This invention relates to the cytosolic translocation factor complex (CTL) responsible for the translocation of the catalytic domain of diphtheria toxin from the lumen of endosomes to the cytosol.

Diphtheria toxin (DT) (58 kDa) is a typical single chain AB toxin composed of three functional domains: the amino terminal catalytic (C) domain corresponds to fragment A (21 kDa), and the transmembrane (T) and carboxy terminal receptor binding (R) domains comprise fragment B (37 kDa) of the toxin (Choe et al., *Nature* 357: 216-22, 1992). A disulfide bond between Cys186 and Cys201 subtends a protease sensitive loop and connects fragment A with fragment B. Furin mediated cleavage within this loop and retention of the disulfide bond have been shown to be pre-requisites for intoxication of eukaryotic cells (Tsuneoka et al., *J. Biol. Chem.* 268:26461-5, 1993; Ariansen et al., *Biochem.* 32:83-90, 1993). Substitution of the native R domain with human interleukin-2 (IL-2) has resulted in the formation of a fusion protein toxin, $DAB_{389}$IL-2, whose cytotoxic action is specifically targeted only to cells expressing the high affinity IL-2 receptors (Bacha et al., *J. Exp. Med.* 167:612-622, 1988; Waters et al., *Eur. J. Immunol.* 20:785-91, 1990; Ratts and vanderSpek, *Diphtheria Toxin: Structure Function and its Clinical Applications. In Chimeric Toxins*, H. Lorberboum-Galski, P. Lazarovici, eds., Taylor and Francis, London, New York. p. 14-36, 2002).

The intoxication of eukaryotic cells by diphtheria toxin follows an ordered series of interactions between the toxin and the cell which leads to inhibition of protein synthesis and cell death (Love and Murphy, *Gram-Positive Pathogens*, American Society for Microbiology, Washington, D.C., V. A. Fischetti, J. Rood Ed. pp. 573-582, 2000). Biochemical, genetic and X-ray crystallographic analysis of the toxin has shown the protein to be composed of three distinct domains: an N-terminal catalytic domain (C-domain), a central transmembrane domain (T-domain), and the C-terminal receptor binding domain (R-domain). The intoxication process is initiated by the binding of the toxin to its cell surface receptor, a heparin binding epidermal growth factor-like precursor and CD9. Once bound to its receptor, the toxin is internalized by receptor-mediated endocytosis into an early endsosomal compartment (Moya et al., *J. Cell. Biol.*, 101:548, 1985). Upon acidification of the endosomal lumen by vesicular (v)-

ATPase, the T-domain undergoes a conformational change and spontaneously inserts into the vesicle membrane forming an 18-22 Å pore or channel (Kagan et al., *Proc. Natl. Acad. Sci., USA,* 78:4950, 1981; Donovan et al., *Proc. Natl. Acad. Sci., USA,* 78:172, 1981). The C-domain, in a fully denatured form, is then specifically thread through this channel and released into the cytosol. Once the C-domain is refolded into an active conformation it catalyzes the $NAD^+$-dependent ADP-ribosylation of elongation factor 2 (EF-2), causing irreversible inhibition of protein synthesis and death of the cell by apoptosis (Pappenheimer, *Annu. Rev. Biochem.*, 46:69, 1977; Kochi and Collier, *Exp. Cell. Res.*, 208:296, 1993).

The requirements for C-domain translocation of diphtheria toxin across endosomal membranes have been partially defined in PCT patent application publication number WO2005014798. In general, non-toxic mutants of diphtheria have fallen into one of two categories: point mutants that no longer catalyze the $NAD^+$-dependent ADP-ribosylation of elongation factor 2 (e.g., CRM197; see Uchida, *J. Biol. Chem.* 248:3838, 1973) and premature chain termination mutants that are no longer capable of binding to the eukaryotic cell surface receptor for the toxin (e.g., CRM45; see Uchida, vide supra). The construction, isolation, and properties of a series of site-directed mutations in transmembrane helix 1 of $DAB_{389}$IL-2 have been previously reported (vanderSpek et al., *Protein Eng.* 7:985, 1994). In this series, the non-toxic $DAB_{389}$(L221E)IL-2 mutant was of particular interest since it was both ADP-ribosyltransferase positive and bound to the targeted high affinity IL-2 receptor with an affinity equal to that of the wild type fusion protein. It was also found that $DAB_{389}$IL-2 binds with greater affinity to its receptor compared to native DT. Therefore, this fusion protein toxin has proven to be an effective probe for studying internalization of the C-domain by target cells (Williams et al., *J. Biol. Chem.* 265:11885-9, 1990).

While much is known about the mechanisms of receptor binding and receptor mediated endocytosis of native DT and the DT-related fusion proteins, less is known about the precise molecular mechanisms of C-domain translocation across the endosomal membrane and its release into the cytosol.

SUMMARY OF THE INVENTION

We hypothesize that there is a common mechanism of catalytic domain entry for bacterial toxins such as, for example, diphtheria, anthrax lethal factor, anthrax lethal edema factor, and the seven serotypes of botulinum toxin, as well as viral transcription factors, such as, for example, HIV-1 reverse transcriptase and Tat, and that that process requires both a cytosolic translocation factor (CTF) complex that includes β-COP (coatomer beta-subunit), heat shock protein-90 (Hsp90), thioredoxin reductase (TrR-1), and components of the outer surface of endocytic vesicles. Described herein are compounds that include a consensus peptide sequence (the entry motif) held in common by these toxins. When administered to an infected cell, these compounds can bind to the CTF and inhibit the translocation of DT, or other similar toxins, to the cytosol of the cell, thereby moderating or inhibiting cellular intoxication.

Accordingly, the invention features a compound of formula I:

$$X\text{-}AA^{215}\text{-}AA^{216}\text{-}AA^{217}\text{-}AA^{218}\text{-}AA^{219}\text{-}AA^{220}\text{-}AA^{221}\text{-}AA^{222}\text{-}AA^{223}\text{-}AA^{224}\text{-}Y \quad (I),$$

or a pharmaceutically acceptable salt thereof, where X is H or a chain of from 1 to 5 amino acid residues, substituted at the N-terminus with a nitrogen protecting group, $R^1$—C(O)—, or H; Y is OH, $NH_2$, $NHR^2$, $NHR^2R^3$, $OR^4$, or a chain of from 1 to 5 amino acid residues, substituted at the C-terminus with OH, $NH_2$, $NHR^2$, $NHR^2R^3$, or $OR^4$, wherein $R^1$ is a $C_{1-6}$ alkyl, $C_6$ or $C_{10}$ aryl, $C_{1-9}$ heterocyclyl, $C_{1-6}$ alkoxy, $C_{7-16}$ aralkyl, $C_{2-15}$ heterocyclylalkyl, $C_{7-16}$ aralkoxy, $C_{2-15}$ heterocyclyloxy, or a polyethylene glycol moiety; each of $R^2$ and $R^3$ is, independently, H, a $C_{1-6}$ alkyl, $C_6$ or $C_{10}$ aryl, $C_{1-9}$ heterocyclyl, $C_{7-16}$ aralkyl, $C_{2-15}$ heterocyclylalkyl, or a polyethylene glycol moiety; $R^4$ is H, $C_{1-6}$ alkyl, $C_6$ or $C_{10}$ aryl, $C_{1-9}$ heterocyclyl, $C_{1-6}$ alkoxy, $C_{7-16}$ aralkyl, $C_{2-15}$ heterocyclylalkyl, a carboxyl protecting group, or a polyethylene glycol moiety; $AA^{215}$ is Thr, Ser, Gly, or Leu; $AA^{216}$ is Gln; $AA^{217}$ is Ile, Leu, or Val; $AA^{218}$ is Glu; $AA^{219}$ is Asn; $AA^{220}$ is Leu or Ile; $AA^{221}$ is Lys or Arg; $AA^{222}$ is Glu, Asn, or Asp; $AA^{223}$ is Lys, H is, Ser, Ile, or Asn; and $AA^{224}$ is Gly, Leu, Val, Met, or Ile.

In one embodiment, $AA^{215}$ is Thr; $AA^{216}$ is Gln; $AA^{217}$ is Ile; $AA^{218}$ is Glu; $AA^{219}$ is Asn; $AA^{220}$ is Leu; $AA^{221}$ is Lys; $AA^{222}$ is Glu; $AA^{223}$ is Lys; and $AA^{224}$ is Gly. In another embodiment, X is $X^a$-Arg-Asp-Lys-Thr-Lys- and Y is -Pro-Ile-Lys-Asn-Ser-$Y^a$, where $X^a$ is $R^1$—C(O)— or H, $Y^a$ is OH, $NH_2$, $NHR^2$, $NHR^2R^3$, or $OR^4$. In yet another embodiment, the compound of formula I is $X^a$-Arg-Asp-Lys-Thr-Lys-Thr-Lys-Ile-Glu-Ser-Leu-Lys-Glu-His-Gly-Pro-Ile-Lys-Asn-Ser-$Y^a$, where each of $X^a$ and $Y^a$ is as previously defined.

For any of the compounds of the inventions, each $R^1$, $R^2$, or $R^4$ can be a polyethylene glycol moiety selected from the group consisting of: $H_3C(OCH_2CH_2)_{cc}OCH_2C(O)$—, $H(OCH_2CH_2)_{cc}OCH_2C(O)$—, $H_3C(OCH_2CH_2)_{cc}OC(O)$—, $H(OCH_2CH_2)_{cc}OC(O)$—, $H_3C(OCH_2CH_2)_{cc}NHC(O)$—, $H(OCH_2CH_2)_{cc}NHC(O)$—, $H_3C(OCH_2CH_2)_{cc}NHC(S)$—, $H(OCH_2CH_2)_{cc}NHC(S)$—, $H_3C(OCH_2CH_2)_{cc}(O)$—, $H(OCH_2CH_2)_{cc}C(O)$—, $H_3C(OCH_2CH_2)_{cc}NHCH_2C(O)$—, $H(OCH_2CH_2)_{cc}NHCH_2C(O)$—, $H_3C(OCH_2CH_2)_{cc}OC(O)C(CH_3)_2$—, and $H(OCH_2CH_2)_{cc}OC(O)C(CH_3)_2$—, where cc is a range of numbers that results in an average molecular weight of the polyethylene glycol moiety of between 1,000-40,000, preferably 20,000 or 40,000, or a polyethylene glycol moiety selected from the group consisting of: maleimide-$(CH_2)_{bb}C(O)NHCH_2CH_2(OCH_2CH_2)_{aa}OCH_2C(O)$—, maleimide-$(CH_2)_{bb}C(O)NHCH_2CH_2(OCH_2CH_2)_{aa}NHCH_2C(O)$—, maleimide-$(CH_2)_{bb}C(O)NHCH_2CH_2(OCH_2CH_2)_{aa}NHC(S)$—, maleimide-$(CH_2)_{bb}NHC(S)$, maleimide-$(CH_2)_{bb}C(O)$—, or maleimide-$(CH_2)_{bb}$—, where aa is 1-10 and bb is 1-4.

For those compounds that contain a polyethylene glycol chain that includes a maleimide functional moiety, the compound can be further reacted with a monoclonal antibody, or fragment thereof, to form a covalent bond between a sulfur atom of the antibody and the maleimide moiety of the compound.

By selectively inhibiting the catalytic domain of toxins or viral factors from translocating across endosomal membranes, the compounds of the invention, or derivatives or peptidomimetics thereof, can inhibit mammalian cell death caused by such toxins/factors. Therefore, these compounds can be used in the prophylaxis or treatment of diseases caused by toxin-producing bacteria or in the prophylaxis or treatment of adverse events that are caused by the direct exposure of mammals to toxins or toxin derivatives, such as, for example, fusion toxin-proteins. The compounds of the invention can also be used for the prophylaxis or treatment of viral diseases by inhibiting the translocation across endosomal membrane of viral/retroviral transcription factors.

Accordingly, in another aspect, the invention features the use of any of the compounds of the invention in the manufacture of a medicament for inhibiting cell death in a mammal, preferably a human. In one embodiment, the compound inhibits the translocation of a viral or bacterial toxin from the lumen of an endosome to the cytosol of said cell. In one example the toxin is an AB toxin, such as, for example Diphtheria toxin, a Botulinum toxin, Anthrax toxin LF, or Anthrax toxin EF. In another embodiment, the compound inhibits the translocation of a viral or retroviral transcription factor, such as, for example, human immunodeficiency virus (HIV-1) reverse transcriptase or Tat.

In another aspect, the invention features a compound having a nucleic acid sequence encoding any of the peptide sequences of the invention (those peptides represented by the $AA^{215}$-$AA^{224}$ peptide sequence formula I). The peptide sequence can be one selected from the group consisting of: Thr-Lys-Thr-Gin-Ile-Glu-Gln-Leu-Lys-Glu-Lys-Gly; Arg-Asp-Lys-Thr-Lys-Thr-Gln-Ile-Glu-Gln-Leu-Lys-Glu-Lys-Gly-Pro-Ile-Lys-Asn-Lys; Asp-Trp-Asp-Val-Ile-Arg-Asp-Lys-Thr-Lys-Thr-Gln-Ile-Glu-Gln-Leu-Lys-Glu-Lys-Gly; and Arg-Asp-Lys-Thr-Lys-Thr-Lys-Thr-Gln-Ile-Glu-Gln-Leu-Lys-Glu-Lys-Gly-Pro-Ile-Lys-Asn-Lys. The peptide sequence can also be Arg-Asp-Lys-Thr-Lys-Thr-Lys-Ile-Glu-Ser-Leu-Lys-Glu-His-Gly-Pro-Ile-Lys-Asn-Ser.

In another embodiment the nucleic acid is operably linked to an inducible promoter. Examples of inducible promoter systems include those where the expression of the peptide sequence can moderated by treating the transfected cell with an agent selected from the group consisting of: doxycycline; retinal; cyclosporin or analogs thereof; FK506; FK520; and rapamycin or analogs thereof.

In another aspect, the invention features a pharmaceutical composition of a compound of the invention. In one embodiment, the pharmaceutical composition can include agents or compounds that facilitate delivery of the peptides to therapeutic targets. Such delivery strategies are described in *Therapeutic Protein and Peptide Formulation and Delivery* (ACS Symposium Series, No 675) (1997), edited by Shahrokh, et al. and in *Formulation and Delivery of Proteins and Peptides* (ACS Symposium Series, No 567) (1994), edited by Cleland and Langer, both of which are hereby incorporated by reference.

In another aspect, the invention features a method of determining whether a compound is capable of inhibiting cell death in a mammal, with the method including following steps: a) isolating endosomes, desirably early endosomes, from a cell, b) placing the endosomes in a cytosolic buffer, c) contacting the endosomes with a fusion protein-toxin, wherein the protein includes a binding moiety for a component of the cell membrane of the cell and the toxin includes a fragment of Diphtheria toxin, d) contacting the endosomes with a cytosolic translocation factor complex that includes β-COP, e) contacting the endosomes with the compound, and f) measuring translocation of the toxin, where a decreased level of the translocation relative to that observed in the absence of the compound indicates that the compound inhibits cell death.

In another aspect, the invention features a method of determining whether a compound is capable of promoting cell death in a mammal, with the method including the following steps: a) isolating endosomes, desirably early endosomes, from the cell, b) placing the endosomes in a cytosolic buffer, c) contacting the endosomes with a fusion protein-toxin, wherein the protein includes a binding moiety for a component of the cell membrane of the cell and the toxin includes a fragment of Diphtheria toxin, d) contacting the endosomes with a cytosolic translocation factor complex that includes β-COP, e) contacting the endosomes with the compound, and f) measuring translocation of the toxin, where an increased level of translocation relative to that observed in the absence of the compound indicates that the compound inhibits cell death.

The protein portion of the fusion protein-toxin can be any protein or protein fragment that binds to a component of mammalian cellular membranes and is subsequently internalized. In a desirable embodiment, the protein is IL-2. Other examples include monoclonal antibodies that bind to cellular membrane epitopes. In a most desirable embodiment, the fusion protein-toxin is $DAB_{389}$IL-2 (vanderSpek et al., *J. Biol. Chem.* 269(34):21455-9, 1994). In another embodiment, the cytosolic translocation factor includes Hsp 90 and thioredoxin reductase. Assessing translocation can include measuring the ADP-ribosylation of elongation factor-2.

In another aspect, the invention features a composition that contains coatomer, beta subunit (β-COP), or a protein that is substantially identical to β-COP, complexed to a cellular fraction, where the composition is formed by adding β-COP to the cytosol of a mammalian cell, has a molecular weight of between 100 kDa and 250 kDa, and facilitates the translocation of the fusion protein $DAB_{389}$IL-2 from the interior to the exterior of endosomes. In one embodiment, the β-COP that is added is a human recombinant protein. In another embodiment Hsp 90 is also part of the composition. In yet another embodiment, the composition includes TrR-1 and Hsp 90, where both of these components are human recombinant proteins.

In yet another aspect the invention features an interference-nucleotide, such as, for example an iRNA or siRNA, adapted to inhibit or decrease transcription or translation of a factor(s) that is part of the CTF complex (e.g., β-COP, Hsp-90, and TrR-1).

Abbreviations and Definitions

The following abbreviations are used throughout the application: "br" stands for bovine recombinant; when not referring to the amino acid cysteine, "C" stands for catalytic; "CTF" stands for cytosolic translocation factor; "DT" stands for diphtheria toxin; "EF-2" stands for Elongation Factor 2; "ESI" stands for electrospray ionization; "hr" stands for human recombinant; "Hsp" stands for heat shock protein; "MALDI" stands for matrix assisted laser desorption ionization; "MS" stands for mass spectrometry; when not referring to the amino acid threonine, "T" stands for transmembrane; "TrR-1" stands for: thioredoxin reductase; "v" stands for vesicular.

The terms "alkoxy" or "alkyloxy," as used interchangeably herein, represent an alkyl group attached to the parent molecular group through an oxygen atom. Exemplary unsubstituted alkoxy groups are of from 1 to 6 carbons.

The term "alkyl," as used herein, represents a monovalent group derived from a straight or branched chain saturated hydrocarbon of, unless otherwise specified, from 1 to 6 carbons and is exemplified by methyl, ethyl, n- and isopropyl, n-, sec-, iso- and tert-butyl, neopentyl and the like and may be optionally substituted with one, two, three or, in the case of alkyl groups of two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy; (7) aryloyl; (8) azido; (9) carboxaldehyde; (10) cycloalkyl of three to eight carbon atoms; (11) halo; (12) heterocyclyl; (13) (heterocycle)oxy; (14) (heterocycle)oyl; (15) hydroxyl; (16) N-protected amino; (17) nitro; (18) oxo; (19) spiroalkyl of three to eight carbon atoms; (20) thioalkoxy of one to six carbon atoms; (21) thiol; (22) —$CO_2R^A$, wherein $R^A$ is selected from the group consisting of (a) alkyl, (b) aryl and (c) arylalkyl, wherein the alkylene group is of one to six carbon atoms; (23) —C(O)$NR^BR^C$, wherein $R^B$ and $R^C$ are independently selected from the group consisting of (a) hydrogen, (b) alkyl, (c) aryl and (d) arylalkyl, wherein the alkylene group is of one to six carbon atoms; (24) —$SO_2R^D$, wherein $R^D$ is selected from the group consisting of (a) alkyl, (b) aryl and (c) arylalkyl, wherein the alkylene group is of one to six carbon atoms; (25) —$SO_2NR^ER^F$, wherein $R^E$ and $R^F$ are independently selected from the group consisting of (a) hydrogen, (b) alkyl, (c) aryl and (d) arylalkyl, wherein the alkylene group is of one to six carbon atoms; and (26) —$NR^GR^H$, wherein $R^G$ and $R^H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group.

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl and the like and may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, wherein the alkyl and alkylene groups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfonylalkyl, wherein the alkyl and alkylene groups are independently of one to six carbon atoms; (9) aryl; (10) arylalkyl, wherein the alkyl group is of one to six carbon atoms; (11) amino; (12) aminoalkyl of one to six carbon atoms; (13) aryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde)alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —$(CH_2)_qCO_2R^A$, wherein q is zero to four and $R^A$ is selected from the group consisting of (a) alkyl, (b) aryl and (c) arylalkyl, wherein the alkylene group is of one to six carbon atoms; (37) —$(CH_2)_qCONR^BR^C$, wherein $R^B$ and $R^C$ are independently selected from the group consisting of (a) hydrogen, (b) alkyl, (c) aryl and (d) arylalkyl, wherein the alkylene group is of one to six carbon atoms; (38) —$(CH_2)_qSO_2R^D$, wherein $R^D$ is selected from the group consisting of (a) alkyl, (b) aryl and (c) arylalkyl, wherein the alkylene group is of one to six carbon atoms; (39) —$(CH_2)_qSO_2NR^ER^F$, wherein $R^E$ and $R^F$ are independently selected from the group consisting of (a) hydrogen, (b) alkyl, (c) aryl and (d) arylalkyl, wherein the alkylene group is of one to six carbon atoms; (40) —$(CH_2)_qNR^GR^H$, wherein $R^G$ and $R^H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The terms "arylalkoxy" or "aralkoxy," as used interchangeably herein, represent an arylalkyl group attached to the parent molecular group through an oxygen atom. Exemplary unsubstituted arylalkoxy groups are of from 7 to 16 carbons.

The terms "arylalkyl" or "aralkyl," as used interchangeably herein, represent an aryl group attached to the parent molecular group through an alkyl group. Exemplary unsubstituted arylalkyl groups are of from 7 to 16 carbons.

The term "heteroaryl," as used herein, represents that subset of heterocycles, as defined herein, which are aromatic: i.e., they contain 4n+2 pi electrons within the mono- or multicyclic ring system. Exemplary unsubstituted heteroaryl groups are of from 1 to 9 carbons.

The terms "heterocycle" or "heterocyclyl," as used interchangeably herein represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocycle" also includes bicyclic, tricyclic and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring such as indolyl, quinolyl, isoquinolyl, tetrahydroquinolyl, benzofuryl, benzothienyl and the like. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroinidolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

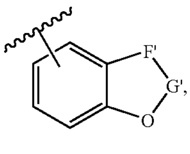

wherein

F' is selected from the group consisting of —$CH_2$—, —$CH_2O$— and —O—, and G' is selected from the group consisting of —C(O)— and —$(C(R')(R''))_v$—, wherein R' and R'' are independently selected from the group consisting of hydrogen or alkyl of one to four carbon atoms, and v is one to three and includes groups such as 1,3-benzodioxolyl, 1,4-benzodioxanyl and the like. Any of the heterocycle groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, wherein the alkyl and alkylene groups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfonylalkyl, wherein the alkyl and alkylene groups are independently of one to six carbon atoms; (9) $C_{6-10}$ aryl; (10) arylalkyl, wherein the alkyl group is of one to six carbon atoms; (11) amino; (12) aminoalkyl of one to six carbon atoms; (13) $C_{2-9}$ heteroaryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde)alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocycle; (25) (heterocycle)oxy; (26) (heterocycle)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —$(CH_2)_qCO_2R^A$, wherein q is zero to four and $R^A$ is selected from the group consisting of (a) alkyl, (b) aryl and (c) arylalkyl, wherein the alkylene group is of one to six carbon atoms; (37) —$(CH_2)_qCONR^BR^C$, wherein $R^B$ and $R^C$ are independently selected from the group consisting of (a) hydrogen, (b) alkyl, (c) aryl and (d) arylalkyl, wherein the alkylene group is of one to six carbon atoms; (38) —$(CH_2)_qSO_2R^D$, wherein $R^D$ is selected from the group consisting of (a) alkyl, (b) aryl and (c) arylalkyl, wherein the alkylene group is of one to six carbon atoms; (39) —$(CH_2)_qSO_2NR^ER^F$, wherein $R^E$ and $R^F$ are independently selected from the group consisting of (a) hydrogen, (b) alkyl, (c) aryl and (d) arylalkyl, wherein the alkylene group is of one to six carbon atoms; (40) —$(CH_2)_qNR^GR^H$, wherein $R^G$ and $R^H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "heterocyclylalkyl" represents a heterocycle group, as defined herein, attached to the parent molecular group through an alkyl group. Exemplary unsubstituted heterocyclylalkyl groups are of from 2 to 15 carbons.

The terms "heterocyclyloxy" or "(heterocycle)oxy," as used interchangeably herein, represents a heterocycle group, as defined herein, attached to the parent molecular group through an oxygen atom. Exemplary unsubstituted heterocyclyloxy groups are of from 1 to 9 carbons.

The term "amino acid residue," as used herein, represents a —$N(R^A)C(R^B)(R^C)C(O)$— linkage, wherein $R^A$ is selected from the group consisting of (a) hydrogen, (b) alkyl, (c) aryl and (d) arylalkyl, as defined herein; and $R^B$ and $R^C$ are independently selected from the group consisting of: (a) hydrogen, (b) optionally substituted alkyl, (c) optionally substituted cycloalkyl, (d) optionally substituted aryl, (e) optionally substituted arylalkyl, (f) optionally substituted heterocyclyl, and (g) optionally substituted heterocyclylalkyl, each of which is as defined herein. For natural amino acids, $R^B$ is H and $R^C$ corresponds to those side chains of natural amino acids found in nature, or their antipodal configurations. Exemplary natural amino acids include alanine, cysteine, aspartic acid, glutamic acid, phenylalanine, glycine, histidine, isoleucine, lysine, leucine, methionine, aspartamine, ornithine, proline, glutamine, arginine, serine, threonine, valine, tryptophan, and tyrosine, each of which, except glycine, as their D- or L-form. As used herein, for the most part, the names of naturally-occurring amino acids and aminoacyl residues used herein follow the naming conventions suggested by the IUPAC Commission on the Nomenclature of Organic Chemistry and the IUPAC-IUB Commission on Biochemical Nomenclature as set out in Nomenclature of α-Amino Acids (Recommendations, 1974), Biochemistry, 14 (2), (1975). Compounds of the present invention include non-naturally occurring (i.e., unnatural) amino acid residues in their D- or L-form such as, for example, homophenylalanine, phenylglycine, cyclohexylglycine, cyclohexylalanine, cyclopentyl alanine, cyclobutylalanine, cyclopropylalanine, cyclohexylglycine, norvaline, norleucine, ornithine, thiazoylalanine (2-, 4- and 5-substituted), pyridylalanine (2-, 3- and 4-isomers), naphthalalanine (1- and 2-isomers) and the like. Stereochemistry is as designated by convention, where a bold bond indicates that the substituent is oriented toward the viewer (away from the page) and a dashed bond indicates that the substituent is oriented away from the viewer (into the page). If no stereochemical designation is made, it is to be assumed that the structure definition includes both stereochemical possibilities.

What is meant by "cytosolic buffer" is any buffering system into which endosomes can be placed where they remain intact and viable. In one example; 3% sucrose in 100 mM HEPES-KOH pH 7.9, 1.4 mM KCl, 30 mM $MgCl_2$, 2 mM EDTA, and 5 mM DTT constitutes a cytosolic buffer.

What is meant by "cytosolic translocation factor complex" is a group of component proteins that includes β-COP, Hsp 90 and TrR-1, with the complex also having the ability to facilitate the translocation of the catalytic domain of diphtheria toxin from the interior to the exterior of an endosome.

By a "pharmaceutically acceptable excipient" is meant a carrier that is physiologically acceptable to the treated mammal while retaining the therapeutic properties of the compound with which it is administered. One exemplary pharmaceutically acceptable excipient is physiological saline. Other physiologically acceptable excipients and their formulations are known to one skilled in the art and described, for example, in "Remington: The Science and Practice of Pharmacy" (20th ed., ed. A. R. Gennaro A R., 2000, Lippincott Williams & Wilkins).

By "operably linked" is meant that a nucleic acid molecule and one or more regulatory sequences (e.g., a promoter) are connected in such a way as to permit expression and/or secretion of the product (i.e., a polypeptide) of the nucleic acid molecule when the appropriate molecules (e.g., transcriptional activator proteins) are bound to the regulatory sequences.

By "polypeptide" or "peptide" is meant any chain of from 2 to 100 natural or unnatural amino acids, regardless of post-translational modification (e.g., glycosylation or phosphorylation), constituting all or part of a naturally-occurring or non-naturally occurring polypeptide or peptide, as is described herein. Naturally occurring amino acids are any one of the following, alanine (A or Ala), cysteine (C or Cys), aspartic acid (D or Asp), glutamic acid (E or Glu), phenylalanine (F or Phe), glycine (G or Gly), histidine (H, or His), isoleucine (I or Ile), lysine (K or Lys), leucine (L or Leu), methionine (M or Met), asparagine (N or Asn), ornithine (O or Orn), proline (P or Pro), hydroxyproline (Hyp), glutamine (Q or Gln), arginine (R or Arg), serine (S or Ser), threonine (T or Thr), valine (V or Val), tryptophan (W or Trp), or tyrosine (Y or Tyr).

By "substantially identical" is meant a protein, polypeptide, or nucleic acid exhibiting at least 75%, but preferably 85%, more preferably 90%, most preferably 95%, or even 99% identity to a reference amino acid or nucleic acid sequence. For polypeptides, the length of comparison sequences will generally be at least 10 amino acids, and preferably at least 20 amino acids. For nucleic acids, the length of comparison sequences will generally be at least 30 nucleotides, preferably at least 60 nucleotides, and more preferably at least 120 nucleotides.

DETAILED DESCRIPTION

Figure 1:
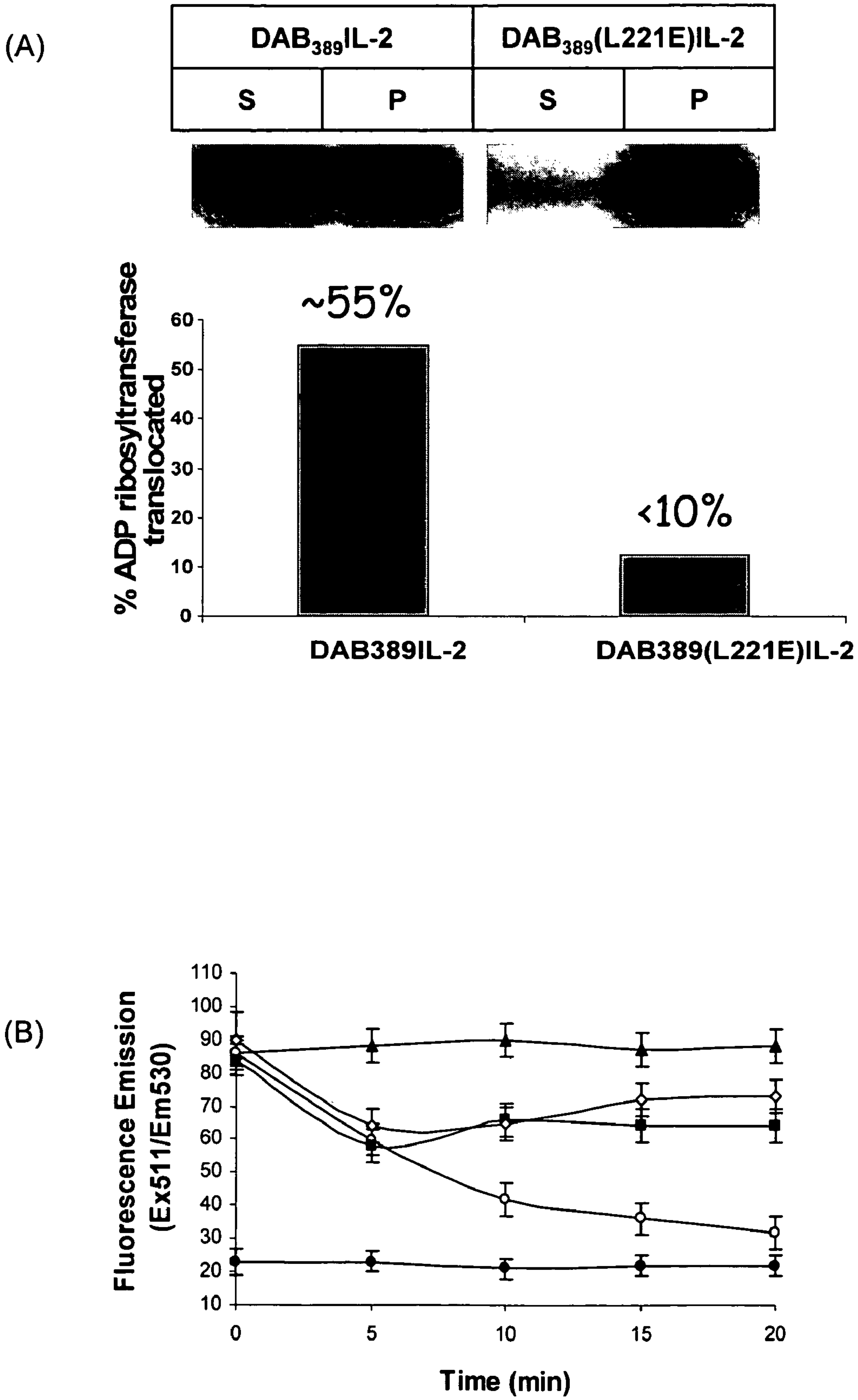
FIG. 1A shows autoradiographs of the in vitro translocation of the C-domain from either $DAB_{389}$IL-2 or $DAB_{389}$(L221E)IL-2 (the non-toxic, translocation deficient mutant) from the lumen of early endosomes to the external milieu, assayed as previously described by Ratts et al. (*J. Cell Biol.* 160:1139, 2003). In this assay, the early endosomal compartment of Hut102/6TG cells was pre-loaded with fusion protein toxin in the presence of Bafilomycin A1. Following cell lysis and partial purification of early endosomes by sucrose density gradient centrifugation, the specific translocation of the C-domain to the external milieu was determined after the addition of both ATP (A) and either crude cytosol (C) or partially purified cytosolic translocation factor (ppCTF) complex to the reaction mixture. ADP-ribosyltransferase activity associated with the pellet (P) and supernatant fluid fractions were monitored by autoradiography following incorporation of [$^{32}$P]-ADP-ribose into elongation factor 2.
FIG. 1B is a graph showing the sensitivity of Hut102/6TG and Hut102/6TG-T1 cells to $DAB_{389}$IL-2 by dose response analysis. The early endosomal compartment in Hut102/6TG cells was pre-loaded with either Oregon Green (OG) 514 conjugated to 70 kD dextran in the absence or presence of either $DAB_{389}$IL-2 or $DAB_{389}$(L221E)IL-2 in the presence of Bafilomycin A1. Following cell lysis and partial purification of the early endosome fraction by sucrose density gradient centrifugation, endosomes pre-loaded with OG514 dextran conjugate alone were resuspended in translocation buffer in the absence (▲) or presence (○) of 2 mM ATP. Endosomes that were pre-loaded with either OG514 conjugate and $DAB_{389}$IL-2 (■) or OG514 conjugate and $DAB_{389}$(L221E)IL-2 (◇) were resuspended in translocation buffer in the presence of 2 mM ATP. Partially purified early endosomes that were not pre-loaded with OG514-dextran are indicated by the symbol (●). Fluorescence Emission was measured at an excitation wavelength of 511 nm and an emission wavelength of 530 nm. Values were compared to 1 ng/ml OG 514 conjugate standards at pH 7.5 and 4.5.

In the present invention, the in vitro C-domain translocation assay described by Ratts et al. (*J. Cell Biol.* 160:1139, 2003) was used to further characterize the interaction between $DAB_{389}$(L221E)IL-2 and Hut102/6TG cells. In these experiments, early endosomes in Hut102/6TG cells were separately pre-loaded with either $DAB_{389}$IL-2 or $DAB_{389}$(L221E)IL-2 in the presence of Bafilomycin A1. Cells were lysed and early endosomes were partially purified by sucrose density centrifugation. Upon removal of Bafilomycin A1 and the addition of both ATP and partially purified CTF complex, translocation and release of the C-domain from the endosomal lumen to the external milieu was measured by determining the ADP-ribosyltransferase activity in both the pellet and supernatant fluid fractions following ultracentrifugation. Since translocation and refolding of the C-domain into a biologically active conformation have been shown previously to be mutually exclusive events (Ratts et al., vide supra), crude cytosolic extracts were added prior to the ADP-ribosylation assay. As shown in FIG. 1A, approximately 60% of the ADP-ribosyltransferase activity from $DAB_{389}$IL-2 was translocated from the endosomal lumen to the external medium in the 30 min incubation period. In marked contrast, essentially all of the ADP-ribosyltransferase activity from $DAB_{389}$(L221E)IL-2 remained in the pellet fraction, demonstrating that the non-toxic phenotype of this mutant results from a defect in C-domain translocation across the endosomal vesicle membrane and release into the surrounding medium.

In order to further examine whether or not the T-domain of $DAB_{389}$(L221E)IL-2 is capable of inserting into the vesicle membrane and forming ion conductive channels, this peptide was co-internalized with the pH sensitive dye Oregon Green 514 (OG 514) conjugated to high molecular weight dextran (70 kDa) into early endosomes, which were then monitored for acidic pH quenching of the fluorescent signal upon addition of ATP to the reaction mixture. For early endosomes that were pre-loaded with OG515-dextran alone, the fluorescent signal remained constant in the absence of added ATP. For endosomes to which ATP was added, a progressive quenching of the fluorescent signal was observed over time (see FIG. 1B). Co-internalization of OG514-dextran with either $DAB_{389}$IL-2 or $DAB_{389}$(L221E)IL-2 into early endosomes, followed by the addition of ATP to the reaction mixture, resulted in the virtual identical quenching of the fluorescent signal. In both instances, quenching of the fluorescent signal was seen for the first 5 minutes after which the signal remained relatively constant, presumably due to an equilibration of the luminal pH caused by an influx of protons into the endosomal lumen through the continuous action of the v-ATPase proton pump and the efflux of protons to the external milieu through the nascent channel formed by the membrane insertion of the diphtheria toxin T-domain. Taken together, these results suggest that both the wild type and mutant fusion protein toxins are capable of forming ion conductive channels in the endosomal vesicle membrane. These results also suggest that the non-cytotoxic phenotype of $DAB_{389}$(L221E)IL-2 is due to a specific defect in C-domain translocation and release into the cytosol of target cells.

Some AB toxins are known to employ a common route of entry into the cell requiring passage through an acidified early endosomal compartment, (Pappenheimer, *Annu. Rev. Biochem.* 46:69, 1977; Wesche et al., *Biochemistry* 37:15737, 1998; Bade et al., *Naunyn. Schmiedebergs Arch. Pharmacol.* 365:R13, 2002). Further, in all instances where this is so, the putative "translocation motif" is positioned in a region of these protein toxins consistent with their emergence on the cytosolic side of the endosomal membrane early in the delivery process. It is of particular interest to note that the L221E mutation in $DAB_{389}$IL-2, which gives rise to a translocation deficient phenotype as described above, is contained within the most highly conserved region in the motif. In anthrax lethal factor the putative "translocation motif" is positioned between residues 28-39 in the mature protein, a region that is structurally distinct from the protective antigen binding domain (Lacey et al., *J. Biol. Chem.* 277:3006, 2002). In addition, N-terminal deletion analysis of anthrax lethal factor has shown previously that this region is required for toxicity (Arora and Leppla, *Infect. Immun.* 62:4955, 1994). In contrast, this translocation motif was not detected in those protein toxins known to undergo retrograde transport and whose catalytic domains enter the cytosol from the endoplasmic reticulum (e.g., cholera toxin, Shiga toxin, ricin toxin, *Pseudomonas* exotoxin A).

The potential role for the "translocation motif" in mediating delivery of the diphtheria toxin C-domain across early endosomal membrane was further explored by constructing a gene encoding a peptide encompassing amino acids 210-229 of diphtheria toxin. The PCR primer used for the 5'-end of this construct introduced a Kozak sequence and translation initiation signal to ensure expression of the peptide as well as an EcoRI restriction endonuclease site (Kozak, *J. Biol. Chem.* 266:19867, 1991). The PCR primer for the 3' end of the mini-gene included a transcription termination signal and an XbaI restriction endonuclease site. Following PCR amplification and hybridization, double stranded oligonucleotides were digested with EcoRI and XbaI, and ligated into the corresponding restriction sites in the pTRACER CMV2 vector. The TOP10 strain of *E. coli* was then transformed and single colonies were selected on LB agar medium supplemented with 100 μg/mL ampicillin. Individual clones were isolated and plasmid DNA was prepared and sequenced to insure that a single copy of the mini-gene encoding the putative "translocation motif" was inserted in the proper orientation and retained the correct reading frame. A single plasmid preparation was then selected, designated pTRACER-T1, and used to transfect Hut102/6TG cells (see Methods section).

Stable transfectants were selected in the presence of Zeocin, and insertion of pTRACER-T1 DNA into the genome was phenotypically confirmed by both the constitutive expression of green fluorescent protein (GFP) and resistance to Zeocin (data not shown). Individual transfectant cell lines were then isolated by limit dilution. To demonstrate the presence of mRNA specific for T1 mini-gene expression, total mRNA was partially purified from Hut102/6TG and Hut102/6TG-T1 cells and oligonucleotide primers specific for the 5'-end of the T1 mini-gene and 3'-end vector sequences were used for PCR amplification. mRNA encoding the T1 mini-gene was detected in extracts of Hut102/6TG-T1 cells, but not in extracts of the parental Hut102/6TG cell line (data not shown).

Figure 2:
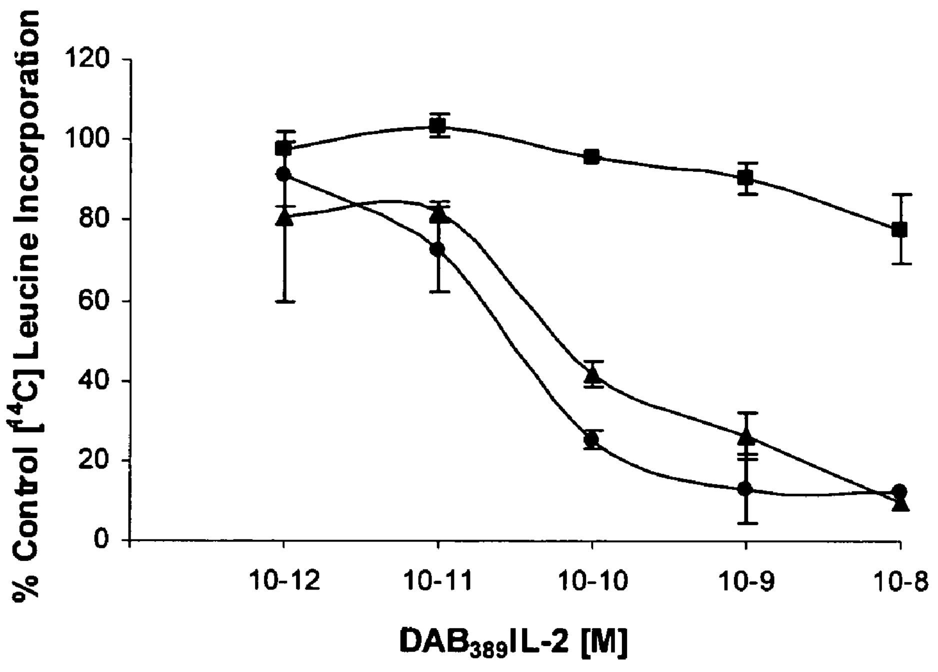
FIG. 2 is a graph showing the dose response of Hut102/6TG (●), Hut102/6TG-T1 (■), and Hut102/6TG-T1/pRR-XT1 (▲) cells to the fusion protein toxin $DAB_{389}$IL-2. Individual cell lines were seeded at $5\times10^4$ cells per well in 96 well plates and incubated in the absence of presence of varying concentrations of $DAB_{389}$IL-2 for 18 hrs at 37° C. in 5% $CO_2$. Cells were then washed and resuspended in minimal (leucine depleted) medium containing [$^{14}$C]-leucine and pulse labeled for 2 hrs at 37° C. in 5% $CO_2$. Cells were then lysed with 0.4M KOH, incubated for 10 min, and total protein was precipitated by the addition of 10% trichloroacetic acid (TCA). Protein precipitates were collected on glass fiber filters (Whatman GF/A) using a PhD cell harvester and radioactivity was measured according to standard methods. Cells incubated in medium alone served as controls. The results from three separate experiments in which each fusion protein toxin concentration was assayed in quadruplicate are presented. Results are presented as percent control level of [$^{14}$C]-leucine incorporation.

Hut102/6TG and Hut102/6TG-T1 cells were then examined for their sensitivity to $DAB_{389}$IL-2 by dose response analysis (see Example 3). As shown in FIG. 2, the $IC_{50}$ for $DAB_{389}$IL-2 in Hut102/6TG cells was found to be $5\times10^{-11}$ M. In marked contrast, the $IC_{50}$ for $DAB_{389}$IL-2 in Hut102/6TG-T1 cells was greater than $10^{-8}$ M. Analogous results were obtained when the parental and transfectant cell lines were challenged with native diphtheria toxin (data not shown).

To further demonstrate that expression of the "translocation motif" mini-gene was directly associated with the toxin resistant phenotype, Hut102/6TG-T1 cells were transfected with plasmid pRR-XT1, which produces siRNA specific for knock down of the "translocation motif" transcripts (see Methods section). Co-expression of siRNA specific for T1 mini-gene expression in Hut102/6TG-T1 cells results in the restoration of full sensitivity to $DAB_{389}$IL-2 ($IC_{50}$~$7\times10^{-11}$M, data not shown). These results demonstrate that the toxin resistant phenotype in Hut102/6TG-T1 cells is directly related to the expression of the "translocation motif" in target cells. Taken together the above observations support the hypothesis that the putative "translocation motif" within transmembrane helix 1 of the diphtheria toxin T-domain plays an essential role in the delivery of the C-domain from the lumen of acidified early endosomes to the cytosol in vivo.

In order to isolate other potential cytosolic T1 binding proteins, a fusion protein between glutathione S-transferase (GST) and diphtheria toxin sequences 140 to 271 was constructed. Following expression and purification of the GST-DT140-271 fusion protein from extracts of recombinant *E. coli*, a series of pull down experiments in post-nuclear supernatant extracts of Hut102/6TG cells were conducted. Following SDS-polyacrylamide gel electrophoresis, immunoblot analysis using an anti-β-COP antibody (obtained from Abcom, Cambridge, UK), revealed individual β-COP-containing proteins that were specifically bound to the DT140-271 portion of the fusion protein (see FIG. 3A). These proteins were further identified by mass spectrometry sequence analysis (data not shown). The identification of β-COP in pull down mixtures was of particular interest since Lemichez et al., *Mol. Microbiol.* 23:445, 1997 demonstrated that C-domain translocation was inhibited by the addition of anti-β-COP to the in vitro translocation reaction mixture.

Figure 3:
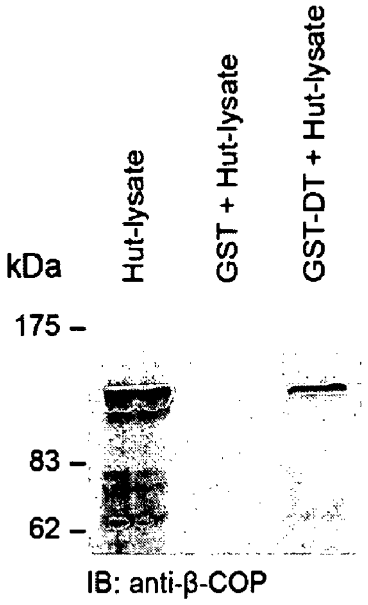
FIG. 3A is an autoradiograph showing the interaction of β-COP with DT140-271 in GST-pull down experiments. GST or the fusion protein GST-DT140-271 was expressed in recombinant *E. coli* and purified by affinity chromatography on glutathione-Sepharose columns. Purified recombinant protein was then applied to GST-beads. Cellular extracts from Hut102/6TG cells were passed over the columns and eluted by the addition of reduced glutathione. Fractions were analyzed by SDS-polyacrylamide gel electrophoresis and immunoblot using anti-β-COP antibodies. (B)
FIG. 3B is a electrophoresis gel showing the interaction of β-COP with GST-DT140-271 in pull down experiments using cellular extracts from Hut102/6TG cells in the absence and presence of increasing concentrations of the synthetic "translocation motif" peptide T1 (SEQ ID NO 2). The concentration of T1 peptide added to the pull down reaction mix is shown in parentheses.
Figure 3:
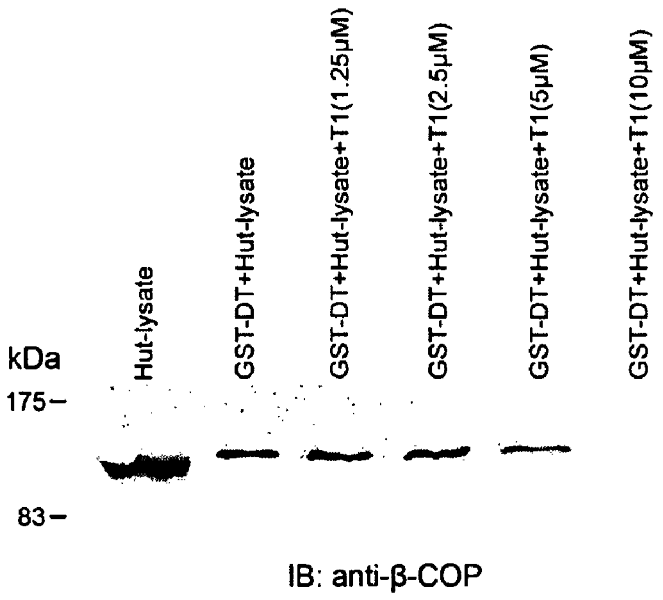

In order to further explore the interaction between β-COP and DT140-271 sequences, the inhibition of this interaction by the addition of the synthetic T1 peptide to the pull down mixture was investigated. In these experiments the T1 peptide was added to post-nuclear supernatant extracts of Hut102/6TG cells and incubated for 1 hr at 4° C., GST-DT140-271 was added and following a 1 hour incubation at 4° C., proteins that were pulled down were separated by electrophoresis on SDS-polyacrylamide gels and analyzed by immunoblot using anti-β-COP. As shown in FIG. 3B, in the absence of the T1 peptide, GST-DT140-271 specifically interacts with and pulls down β-COP from Hut102/6TG extracts. In marked contrast, addition of increasing concentrations of T1 peptide (1.25 μM-10 μM) to the pull down reaction mixture inhibits this interaction in a dose dependent manner. In control experiments a peptide of similar molecular weight and pI as T1, failed to block the pull down of β-COP by GST-DT140-271 (data not shown). Taken together these results strongly suggest that the interaction between β-COP and DT140-271 at least overlaps with the "translocation motif" sequence. In addition, these results also demonstrate that, like Hsp 90 and thioredoxin reductase, β-COP plays a direct role in C-domain translocation from the lumen of early endosomes and serves as an essential component of the cytosolic translocation factor (CTF) complex.

Since the results presented above support the hypothesis that C-domain translocation and release into the cytosol requires assistance of a CTF complex of proteins, it was reasoned that the toxin might carry a specific motif that interacts with one or more of the components of this complex. In an attempt to identify a putative "translocation motif" we compared by BLAST [Basic Local Alignment Search Tool (Altschul et al., *J. Mol. Biol.* 215:403, 1990)] analysis a family of overlapping 12 amino acid sequences, each of which separated by 3 amino acids, of diphtheria toxin against the sequence of other bacterial protein toxins. A consensus sequence for the motif (SEQ ID NO 1) was identified using the Multiple Expectation maximization for Motif Elucidation (MEME) tool (Bailey and Elkan, *Proceedings of the Second International Conference on Intelligent Systems for Molecular Biology*, AAAI Press, Menlo Park, Calif., pp. 28-36, 1994). As shown in Table 1, position-specific-iterated (PSI)-BLAST (Karlin and Altschul, *Proc. Natl. Acad. Sci., USA* 87:2264, 1990) and AlignX (Vector NTI, version 6) computational analysis indicated a statistically significant conserved 10 amino acid peptide motif present in transmembrane helix T1 (TH1) of diphtheria toxin with dodecamer sequences in anthrax lethal and edema factors, as well as the botulinum neurotoxin serotypes A, C, and D.

TABLE 1

Results of position-specific-iterated (PSI)-BLAST and AlignX computational analysis of native diphtheria toxin

| Toxin[1] | Residue numbers | Sequence |
|---|---|---|
| Anthrax Edema Factor (P40136) | 50-65 | EKNK**TEKEKFKDSI**NN |
| Anthrax Edema Factor (P40136) | 404-420 | KLDH**LRIEELKENG**II |
| Anthrax Lethal Factor (YP016503) | 32-47 | ERNK**TQEEHLKEIM**KH |
| Botulinum neurotoxin Serotype A (P10845) | 719-734 | AKVN**TQIDLIRKKM**KE |
| Botulinum neurotoxin Serotype A (P10845) | 828-843 | GTLI**GQVDRLKDKV**NN |
| Botulinum neurotoxin Serotype C1 (P18640) | 755-770 | ENIK**SQVENLKNSL**DV |
| Botulinum neurotoxin Serotype D (P19321) | 751-766 | ENIK**SQVENLKNSL**DV |
| Diphtheria toxin (AAV70486 | 221-236 | DKTK**TKIESLKEHG**PI |
| Consensus | | ----**TQIENLKEKG**-- |

[1]Database ascension numbers are given in parentheses

Compounds of Formula I

The importance of the binding of a conserved peptide sequence found in diphtheria toxin, as well as other toxins, to a cytosolic translocation factor for cellular intoxication has been demonstrated herein. In addition, a consensus sequence for this conserved region has been identified. Accordingly, in a first aspect, the invention features compounds of formula I:

$$X\text{-}AA^{215}\text{-}AA^{216}\text{-}AA^{217}\text{-}AA^{218}\text{-}AA^{219}\text{-}AA^{220}\text{-}AA^{221}\text{-}AA^{222}\text{-}AA^{223}\text{-}AA^{224}\text{-}Y \quad (I),$$

where

X is H or a chain of amino acids of from 1 to 5 residues substituted at the N-terminus with a nitrogen protecting group, $R^1$—C(O)—, or H; Y is OH, $NH_2$, $NHR^2$, $NHR^2R^3$, $OR^4$, or a chain of amino acids of from 1 to 5 residues substituted at the C-terminus with OH, $NH_2$, $NHR^2$, $NHR^2R^3$, or $OR^4$, where $R^1$ is a $C_{1-6}$ alkyl, $C_6$ or $C_{10}$ aryl, $C_{1-9}$ heterocyclyl, $C_{1-6}$ alkoxy, $C_{7-16}$ aralkyl, $C_{2-15}$ heterocyclylalkyl, $C_{7-16}$ aralkoxy, $C_{2-15}$ heterocyclyloxy, or a polyethylene glycol moiety; each of $R^2$ and $R^3$ is, independently, H, a $C_{1-6}$ alkyl, $C_6$ or $C_{10}$ aryl, $C_{1-9}$ heterocyclyl, $C_{7-16}$ aralkyl, $C_{2-15}$ heterocyclylalkyl, or a polyethylene glycol moiety; $R^4$ is H, $C_{1-6}$ alkyl, $C_6$ or $C_{10}$ aryl, $C_{1-9}$ heterocyclyl, $C_{1-6}$ alkoxy, $C_{7-16}$ aralkyl, $C_{2-15}$ heterocyclylalkyl, a carboxyl protecting group, or a polyethylene glycol moiety; $AA^{215}$ is Thr, Ser, Gly, or Leu; $AA^{216}$ is Gln; $AA^{217}$ is Ile, Leu, or Val; $AA^{218}$ is Glu; $AA^{219}$ is Asn; $AA^{220}$ is Leu or Ile; $AA^{221}$ is Lys or Arg; $AA^{222}$ is Glu, Asn, or Asp; $AA^{223}$ is Lys, H is, Ser, Ile, or Asn; and $AA^{224}$ is Gly, Leu, Val, Met, or Ile.

Methods of Inhibiting Cell Death by Administration of Peptides of the Invention

The present invention also provides methods of inhibiting cell death in a mammal, preferably a human, by administering to the cell a compound of the invention, or analog thereof, which inhibits the translocation of the catalytic domain of a toxin from the lumen of endosomes to the cytosol of the cell. In one example, the toxin is an AB toxin, such as, for example Diphtheria toxin, one of the seven serotypes of Botulinum toxin, Anthrax toxin LF, or Anthrax toxin EF. In another embodiment, the compound inhibits the translocation of a viral or retroviral transcription factor, such as, for example, human immunodeficiency virus (HIV-1) reverse transcriptase or Tat. Compounds of the invention include peptide sequences that contain the entry motif consensus sequence. Compounds of the invention also include peptidyl compounds that are further modified to improve their pharmacological properties, as described in detail herein. The invention also features compounds that include nucleic acid sequences that encode a peptide that contains the entry motif consensus peptide sequence and compounds that include nucleic acid sequences that interfere with the translation of translocation factors, such as, for example, β-COP, Hsp 90, and TrR-1.

Modifications of Compounds of Formula I

It is possible to modify the structure of a compound of the invention for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of CTF. Such modified peptides can be produced, for instance, by amino acid substitution, deletion, or addition.

For example, in a compound of the invention that inhibits translocation from the endosome to the cytosol of a cell (e.g., a compound of formula I), it is reasonable to expect that an isolated replacement of a leucine with an isoleucine or valine, an aspartate with a glutamate, a threonine with a serine, or a similar replacement of an amino acid with a structurally related amino acid will not have a major effect on the ability of the peptide to serve as an inhibitor. Conservative replacements or substitutions are those that take place within a family of amino acids that are related in their side chains, and apply to those that result from genetically encoding or those that are synthetically produced. Amino acids can be divided into four families: (1) acidic residues, such as aspartatic acid or glutamic acid; (2) basic residues, such as lysine, arginine, or histidine; (3) nonpolar residues, such as alanine, valine, leucine, isoleucine, proline, phenylalanine, methionine, or tryptophan; and (4) uncharged polar residues, such as glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic residues, such as aspartate, glutamate; (2) basic residues, such as lysine, arginine histidine, (3) aliphatic residues, such as glycine, alanine, valine, leucine, isoleucine, serine, threonine, with serine and threonine optionally be grouped separately as aliphatic-hydroxyl; (4) aromatic residues, such as phenylalanine, tyrosine, tryptophan; (5) amide residues, such as asparagine, glutamine; and (6) sulfur-containing residues, such as cysteine and methionine (see, for example, Biochemistry, 2nd ed., Ed. by L. Stryer, W H Freeman and Co.: 1981). Alternatively, amino acid replacement can be based on steric criteria, e.g. isosteric replacements, without regard for polarity or charge of amino acid sidechains.

Thus, one or more amino acid residues in a compound of the invention can be replaced with another amino acid residue from the same family. Alternatively, in another embodiment, mutations can be introduced randomly along all or part of a nucleic acid encoding a compound of the invention, such as by saturation mutagenesis, and the resultant mutants can be screened for their ability to inhibit translocation, by methods described herein. Following mutagenesis of the nucleic acid encoding the CTF peptide, the peptide can be expressed by any recombinant technology known in the art, and the activity of the peptide can be determined.

The compounds of the present invention include analogs that contain moieties that improve pharmacodynamic properties, such as, for example, those that increase in vivo half-life; or that improve physical properties, such as, for example, increased resistance to in vivo degradation or increased cell-membrane permeability.

In one example, polymer vehicles may be used to modify the compounds of the present invention. Various means for attaching chemical moieties useful as vehicles are currently available, see e.g., Patent Cooperation Treaty ("PCT") International Publication No. WO 96/11953, entitled "N-Terminally Chemically Modified Protein Compositions and Methods." This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kDa") to about 100 kDa, more preferably from about 5 kDa to about 50 kDa. The PEG groups will generally be attached to the compounds of the invention via acylation or reductive alkylation through a reactive group on the PEG moiety (e.g., an aldehyde, amino, isothiocyanate, or an activated carboxylic acid) to a reactive group on the inventive compound (e.g., an amino, or activated carboxyl group).

A useful strategy for the PEGylation of synthetic peptides consists of combining, through forming a conjugate linkage in solution, a peptide and a PEG moiety, each bearing a special functionality that is mutually reactive toward the other. The peptides can be prepared by solid phase synthesis, as described herein. Through selective deprotection strategies, the peptides are "preactivated" with an appropriate functional group at a specific site. The precursors can be purified and fully characterized prior to reacting with the PEG moiety. Ligation of the peptide with PEG usually takes place in aqueous phase and can be easily monitored by reverse phase analytical HPLC. In a desirable embodiment, the PEG moiety contains functionality reactive towards functional groups contained on biomolecules (e.g. proteins, aminoglycosylglycans), making this moiety a heterobifunctional crosslinker. Preferably, the reactive functionality on the PEG moiety is a maleimide, vinyl carbonyl, vinyl sulfonyl group, or alpha-halocarbonyl, and is reacted with a biomolecule containing a free thiol. Such reactions are extremely facile and can be performed at low reactant concentrations, such as are found in in vitro experiments or in vivo.

Other bifunctional agents are known to be useful for cross-linking the peptides or their functional derivatives to a water-insoluble support matrix or to other macromolecular vehicles. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Also included are alkyl linkers such as $—NH—(CH_2)_5C(O)—$. These alkyl linkers may further be substituted by any non-sterically hindering group such as $C_{1-6}$ alkyl, $C_{2-7}$ acyl, halogen (e.g., Cl, Br), CN, $NH_2$, aryl, heterocyclyl, etc.

Other linkers include those made up of amino acids linked together by amide bonds. In one example, the linker is made up of from 1 to 20 amino acids linked by amide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly $(Gly_4$, $(Gly)_5)$, poly(Gly-Ala), and polyalanines. Other specific examples of linkers are: $(Gly)_3Lys(Gly)_4$; $(Gly)_3AsnGlySer(Gly)_2$; $(Gly)_3Cys(Gly)_4$; and GlyProAsnGlyGly. In some examples, the peptide linker is designed to be cleaved in vivo at a specific dipeptide amide bond by proteolytic enzymes.

Polysaccharide polymers are another type of water soluble polymer which may be used for modification of the compounds of the invention. Dextrans are polysaccharide polymers comprised of individual subunits of glucose predominantly linked by $\alpha$1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (see, for example, WO 96/11953 and WO 96/05309). The use of dextran conjugated to therapeutic or diagnostic immunoglobulins has been reported; see, for example, European Patent Publication No. 0 315 456. Dextran of about 1 kD to about 20 kD is preferred when dextran is used as a vehicle in accordance with the present invention.

Other carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

In other examples, a peptide of the invention can be modified by the replacement of one or more peptidyl (—C(O)NR—) linkages (bonds) by a non-peptidyl linkage. Exemplary non-peptidyl linkages are $—CH_2$-carbamate ($—CH_2—OC(O)NR—$), phosphonate, $—CH_2$-sulfonamide ($—CH_2—S(O)_2NR—$), urea (—NHC(O)NH—), $—CH_2$-secondary amine, and alkylated amide [$—C(O)NR^A—$ wherein $R^A$ is alkyl).

In other examples, one or more individual amino acid residues can be modified. Various derivatizing agents are known to react specifically with selected sidechains or terminal residues. For example, lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been performed, with examples including introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl sidechain groups (aspartyl or glutamyl) may be selectively modified by reaction with carbodiimides (R—N═C═N—R') such as 1-cyclohexyl-3-(2-morpholinyl-(4-ethyl) carbodiimide or 1-ethyl-3-(4-azonia-4,4-dimethylpentyl) carbodiimide, followed by reaction with an amine to form an amide.

Compounds Containing Nucleic Acids Encoding Peptide Sequences of the Invention

Cell death in a mammal can be inhibited by administering to the cell a nucleic acid sequence that encodes a peptide that inhibits the translocation of the catalytic domain of a toxin or a transcription factor from the lumen of endosomes to the cytosol of a mammalian cell. Examples are peptides that include the amino acid sequences of SEQ ID NO. 1.

The nucleic acid sequences of the present invention or portions thereof can be inserted into a vector used to propagate the sequences in a cell. Such vectors are introduced into cells (e.g., prokaryotic or eukaryotic), and the cells are propagated to produce multiple copies of the vector. A useful type of vector is an expression vector. Coding regions of the nucleic acid sequences of the present invention or fragments thereof can be inserted into an expression vector under conditions appropriate for expression of the sequences. Such vectors, are introduced into cells (e.g., prokaryotic or eukaryotic cells) under conditions appropriate for expression. In one embodiment, the cell is eukaryotic (e.g., mammalian, avian, insect, or yeast). In a preferred embodiment, the cell is a human cell.

The invention thus provides nucleic acid constructs which encode the various peptide compounds, or fragments thereof, of the invention, various DNA vectors containing those constructs for use in transducing prokaryotic and eukaryotic cells, cells transduced with the nucleic acids, fusion proteins encoded by the above nucleic acids, and target gene constructs.

Each of the nucleic acids of this invention may further contain an expression control sequence operably linked to the coding sequence and may be provided within a DNA vector, e.g., for use in transducing prokaryotic or eukaryotic cells. Some or all of the nucleic acids of a given composition, including any optional nucleic acids, may be present within a single vector or may be apportioned between two or more vectors. In certain embodiments, the vector or vectors are viral vectors useful for producing recombinant viruses containing one or more of the nucleic acids. The recombinant nucleic acids may be provided as inserts within one or more recombinant viruses which may be used, for example, to transduce cells in vitro or cells present within an organism, including a human or non-human mammalian subject. For example, nucleic acids encoding peptides or peptidyl fragments of the present invention may be present within a single recombinant virus or within a set of recombinant viruses, each of which containing one or more of the set of recombinant nucleic acids. Viruses useful for such embodiments include any virus useful for gene transfer, including adenoviruses, adeno-associated viruses (AAV), retroviruses, hybrid adenovirus-AAV, herpes viruses, lenti viruses, etc. In specific embodiments, the recombinant nucleic acid containing the target gene is present in a first virus and one or more or the recombinant nucleic acids encoding the transcription regulatory protein(s) are present in one or more additional viruses. In such multiviral embodiments, a recombinant nucleic add encoding a fusion protein containing a bundling domain and a transcription activation domain, and optionally, a ligand binding domain, may be provided in the same recombinant virus as the target gene construct, or alternatively, on a third virus. It should be appreciated that non-viral approaches (naked DNA, liposomes or other lipid compositions, etc.) may be used to deliver nucleic acids of this invention to cells in a recipient organism.

The invention also provides methods for rendering a cell capable of regulating expression of a target gene which involves introducing into the cell one or more of the nucleic acids of this invention to yield engineered cells which can express the appropriate fusion protein(s) of this invention to regulate transcription of a target gene. The recombinant nucleic acid(s) may be introduced in viral or other form into cells maintained in vitro or into cells present within an organism. The resultant engineered cells and their progeny containing one or more of these recombinant nucleic acids or nucleic acid compositions of this invention may be used in a variety of important applications, including human gene therapy, analogous veterinary applications, the creation of cellular or animal models (including transgenic applications) and assay applications. Such cells are useful, for example, in methods involving the addition of a ligand, preferably a cell permeant ligand, to the cells (or administration of the ligand to an organism containing the cells) to regulate expression of a target gene. Particularly important animal models include rodent (especially mouse and rat) and non-human primate models.

The coding sequence of the polypeptides of the invention can be placed under the control of a strong constitutive or inducible promoter or promoter/enhancer to achieve expression, and preferably secretion, of the polypeptides of the invention. In certain gene therapy applications, the cells are human and a nucleic acid of the present invention is operably linked to an inducible promoter. Such inducible promoters are known to those skilled in the art. For example, the tetracycline-inducible system of Gossen and Bujard (*Proc. Natl. Acad. Sci. USA* 89:5547-5551, 1992; U.S. Pat. No. 5,464,758), has been used to regulate inducible expression of several genes (Furth et al., *Proc. Natl. Acad. Sci. USA* 91:9302-9306, 1994; Howe et al., *J. Biol. Chem.* 270:14168-14174, 1995; Resnitzky et al., *Mol. Cell. Biol.* 14:1669-1679, 1994; Shockett et al., *Proc. Natl. Acad. Sci. USA* 92:6522-6526, 1995). This system uses a chimeric transcription factor, termed tTA, which is composed of the repressor of *Escherichia coli* (*E. coli*) tetracycline-resistance operon (tetR) and the activation domain (carboxyl terminal domain) of virion protein 16 (VP16) of herpes simplex virus (HSV) (Triezebberg et al., *Genes Dev.* 2:718-729, 1988). The gene of interest is placed downstream of a minimal cytomegalovirus (CMV) 1A promoter, derived from the immediate early CMV genes, which is linked to multiple copies of tetO, the binding site for the tetracycline repressor tetR. In the absence of tetracycline, the tetR portion of the transactivator binds the tetO sequences of the promoter and the VP16 portion facilitates transcription. When tetracycline is present, tetracycline binds the tetR portion of tTA, which in turn prevents binding of the tetR portion to the tetO sequence(s) of the promoter, thus inhibiting transcription. Since even low concentrations of tetracycline are sufficient to block tTA function and since most mammalian cells can tolerate tetracycline, this system provides a tightly regulated on/off switch for gene expression that can be controlled by varying the tetracycline concentration to which the cells are exposed. This work has been extended by Yee et al, U.S. Pat. No. 6,432,705, who describe an inducible promoter activated by a multi-chimeric transactivator that is particularly in the expression of retroviral vectors.

A variety of other regulatable expression systems have been described involving allostery-based switches triggered by tetracycline, RU486 or ecdysone, as well as dimerization-based switches triggered by dimerizing agents such as rapamycin, coumermycin, dimers of FK506, synthetic FKBP-binders and/or CsA, or analogs thereof (see, for example, Clackson, *Current Opinion in Chemical Biology* 1:210-218, 1997) U.S. Pat. No. 6,566,073 describes methods for producing target proteins in vivo using fusion proteins containing conditional retention domains. Illustrative examples of ligand binding domain/ligand pairs include retinol binding protein or variants thereof and retinol or derivatives thereof; cyclophilin or variants thereof and cyclosporin or analogs thereof; FKBP or variants thereof and FK506, FK520, rapamycin, analogs thereof or synthetic FKBP ligands.

Compounds of the Invention that are Interference-nucleotides

In another aspect the invention features interference-nucleotides, such as, for example iRNA or siRNA adapted to inhibit or decrease the transcription of factors that are part of the CTF complex (e.g., β-COP, Hsp-90, and TrR-1). These vectors may be produced via standard recombinant techniques, taking into account the published nucleic acid sequence data for such genes (for β-COP see Duden et al., *Cell* 64(3):649-65, 1991; for Hsp 90 see Rebbe et al., *J. Biol. Chem.* 264(25):15006-11, 1989; for thioredoxin reductase see Gadaska et al., FEBS Lett. 303:5-9, 1995), standard cloning and expression vectors, and vectors adapted to deliver genetic material to a subject, or at least one target cell of a subject, that are known to those skilled in the art.

Methods of Screening Biologically Active Compounds

In one example, a method of identifying a compound that inhibits cell death in a mammal includes the following steps: a) isolating endosomes from said cell; b) placing the endosomes in a cytosolic buffer; c) contacting the endosomes with a fusion protein-toxin, wherein the protein comprises a binding moiety for a component of the cell membrane of the cell and the toxin comprises a fragment of diphtheria toxin; d) contacting the endosomes with a cytosolic translocation factor complex; e) contacting the endosomes with the compound; and e) measuring translocation of the toxin, wherein a decreased level of translocation relative to that observed in the absence of the compound indicates that the compound inhibits said cell death.

In another example, a method of identifying a compound that inhibits cell death in a mammal includes the following steps: contacting a mammalian cell or cell population with a fusion protein-toxin, where the protein has a binding moiety for a component of mammalian cellular membranes and where the toxin contains a fragment of diphtheria toxin that includes the catalytic domain; introducing a cytosolic translocation factor complex (e.g., one that includes a compound of the invention) to the cytosol of the cell(s); contacting the cell(s) with a test compound; and measuring cell death relative to a control cell or cell population which has been similarly treated with fusion protein toxin and a cytosolic translocation factor complex, but not treated with the test compound. A decreased rate of cell death in a cell population treated with the test compound indicates that the compound may interfere with translocation of the toxin. This result can be subsequently confirmed in the more sensitive endosome test described above.

In one example, measuring cell death includes a FACS analysis. Introduction of a test compound and/or the CTF complex can be accomplished by treating the cell or cell population with the compound and waiting for passive diffusion through the cell membrane to the cytosol. If necessary, aids to passive transport (e.g., agents that increase cell permeability) can be used. One method for introducing proteins or peptides into the cells of a mammalian cell culture is the Chariot™ reagent (Morris et al., *Nature Biotechnology* 19:1173-1176, 2001; available from Active Motif, Carlsbad, Calif. This reagent quickly and efficiently delivers biologically active proteins, peptides and antibodies directly into cultured mammalian cells at an efficiency of 60-95%. Less than two hours after delivery, live cells can be assayed to determine the effects of the introduced materials, without the need for fixing. In addition to the introduction of the compounds of the invention into the cultured cells, the use of this reagent also aids in the cellular uptake of the compound to be screened, as well as reporter construct. The Chariot reagent can be used in the presence or absence of serum and is independent of the endosomal pathway, which can modify macromolecules during internalization. Additionally, the use of this method for introducing a protein or peptide bypasses the transcription-translation process, which reduces the time required to complete the assay from overnight to less than two hours.

Preparation of Compounds of Formula I

The compounds of formula I may be prepared by either solid or liquid phase methods described and referenced in standard textbooks, or by a combination of both methods. These methods are well known to those skilled in the art, (see, for example, Bodanszky, *The Principles of Peptide Synthesis*, Hafner, Rees, Trost, Lehn, Schleyer, Zahradnik, Eds., Springer-Verlag, Berlin, 1984; Stewart and Young, *Solid Phase Peptide Synthesis*, Pierce Chemical Co., Rockford, Ill., 1984; and U.S. Pat. Nos. 4,105,603; 3,972,859; 3,842,067; and 3,862,925).

During the synthesis of the compounds of the present invention, the functional groups of the amino acid derivatives used in these methods are protected by blocking groups to prevent cross reaction during the amide bond-forming procedure. Examples of suitable blocking groups and their use are described in *The Peptides: Analysis, Synthesis, Biology*, Academic Press, Gross & Meienhofer, Eds., Vol. 3 (1981) and Vol. 9 (1987). The reaction products are isolated and purified by conventional methods, typically by solvent extraction into a compatible solvent, or by using a washing protocol for resin bound intermediates. The products may be further purified by column chromatography or other appropriate methods, including medium pressure or high pressure liquid chromatography.

In one example, compounds of the invention can be conveniently prepared using solid phase synthesis methodology (Merrifield, *J. Am. Chem. Soc.* 85:2149, 1964; Houghten, *Proc. Natl. Acad. Sci. USA* 82:5132, 1985). Solid phase synthesis begins at the carboxy terminus of the compound by attaching a protected amino acid, or other carboxylic acid-containing compound, to an inert solid support. The inert solid support can be any macromolecule capable of serving as an anchor for the C-terminus of the initial amino acid. Typically, the macromolecular support is a cross-linked polymeric resin (e.g. a polyamide or polystyrene resin). In one embodiment, the C-terminal amino acid is coupled to a polystyrene resin to form a benzyl ester. Particularly useful benzyl-type resins, such as trityl resin, chlorotrityl resin, and Wang resin, are those in which the linkage of the carboxy group (or carboxamide) to the resing is acid-lable. A macromolecular support is selected such that the peptide anchor link is stable under the conditions used to deprotect the α-amino group of the blocked amino acids in peptide synthesis. If a base-labile α-protecting group is used, then it is desirable to use an acid-labile link between the peptide and the solid support. For example, an acid-labile ether resin is effective for base-labile Fmoc-amino acid peptide synthesis. Alternatively, a peptide anchor link and α-protecting group that are differentially labile to acidolysis can be used. For example, an aminomethyl resin such as the phenylacetamidomethyl (Pam) resin works well in conjunction with Boc-amino acid peptide synthesis.

After the initial amino acid is coupled to an inert solid support, the α-amino protecting group of the initial amino acid is removed with, for example, trifluoroacetic acid (TFA) in methylene chloride and neutralized in, for example, triethylamine (TEA). Following deprotection of the initial amino acid's α-amino group, the next α-amino and side chain protected amino acid in the synthesis is added. The remaining α-amino protected and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain.

The condensation reaction between two amino acids, or an amino acid and a peptide, or a peptide and a peptide an be carried out according to the usual condensation methods such as the axide method, mixed acid anhydride method, DCC (N,N'-dicyclohexylcarbodiimide) or DIC (N,N'-diisopropylcarbodiimide) methods, active ester method, p-nitrophenyl ester method, BOP (benzotriazole-1-yl-oxy-tris[dimethylamino]phosphonium hexafluorophosphate)method, N-hydroxysuccinic acid imido ester method, O-benzotriazolyl-N,N,N',N'-tetramethyluronium hexafluorophosphate (HBTU) or O-(7-azabenzotriazol-1-yl)-N,N,N',N'-tetramethyluronium hexafluorophosphate (HATU), and Woodward reagent K method.

Alternatively, other functional groups, can be introduced on the liberated N-terminus of the resin. For example, reaction with commercially available carboxylic acids or acid chlorides, sulfonyl chlorides, or isocyanates under standard conditions known in the art produce compounds of the invention containing an amide, sulfonamide, or urea bond, respectively. An alternative to using isocyanates in preparing urea-containing compounds is to activate the deprotected amine terminus with, for example, phosgene, triphosgene, carbonyl di-imidazole, or p-$NO_2$ phenylchloroformate followed by reaction with primary or secondary amines employed in excess.

It is common in both solid-phase and solution-phase synthesis to protect any reactive side-chain groups of the amino acid with suitable protecting groups. Ultimately, these protecting groups are removed after the desired compounds have been sequentially assembled. Also common is the protection of the α-amino group on an amino acid or a fragment while that entity reacts at the carboxy group followed by the selective removal of the α-amino protecting group to allow subsequent reaction to take place at that location. Accordingly, it is common that an intermediate compound is produced which contains each of the amino acid residues located in the desired sequence in the peptide chain with various of these residues having side chain protecting groups attached. These protecting groups are then commonly removed at substantially the same time so as to produce the desired product following cleavage from the resin. Protecting groups and procedure for their use in peptide synthesis are reviewed in Protective Groups in Organic Synthesis, 3d ed., Greene, T. W. and Wuts, P. G. M., Wiley & Sons (New York: 1999).

Suitable protecting groups for α-amino and side chain amino groups are exemplified by benzyloxycarbonyl (abbreviated Z), isonicotinyloxycarbonyl (iNOC), o-chlorobenzyloxycarbonyl [Z(2Cl)], p-nitrobezyloxycarbonyl [Z($NO_2$)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonyethoxycarbonyl (Msc), trifluoroacetyl, phthalyl, formyl, 2-nitrophenylsulfenyl (NPS), diphenylphosphinothioyl (Ppt), and dimethylphosphinothioyl (Mpt) groups, and the like.

Protective groups for the carboxy functional group are exemplified by benzyl ester, (OBz), cyclohexyl ester (Chx), 4-nitrobenzyl ester (ONb), t-butyl ester (OtBu), 4-pyridylmethyl ester (OPic), and the like. It is often desirable that amino acids such as arginine, cysteine, and serine possessing a functional group other than amino and carboxy groups be protected by a suitable protecting group. For example, the guanidino group may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Nds), 1,3,5-trimethylphenysulfonyl (Mts), and 2,3,6-trimethyl-4-methoxyphenylsulfonyl (Mtr), and the like. The thiol group can be protected with p-methoxybenzyl, trityl, and the like.

In one embodiment, the compounds of the invention are synthesized with the help of blocking groups that protect the side chain amide bond-forming substituents of the N-terminal and C-terminal flanking residues. The protecting group or groups used for the side chain amide bond-forming substituents of the N-terminal and C-terminal flanking residues can be the same or different than the protecting group or groups used to block the side chain functional groups of other residues in the peptide. In a preferred embodiment, the protecting group or groups used to block the side chain amide bond-forming substituents is (are) differentially removable with respect to the protecting groups used for other side chain functional groups, i.e. the side chain amide bond-forming substituents can be deprotected without deprotecting the other side chain functional groups, in addition to being differentially removable with respect to the α-amino protecting group used in peptide synthesis. In another preferred embodiment, the side chain amide bond-forming substituents of the flanking residues are orthogonally protected with respect to each other such that the side chain amide bond-forming substituent of one flanking residue can be deprotected without deprotecting the side chain amide bond-forming substituent of the other flanking residue.

Suitable protecting groups for use in orthogonally protecting the side chain amide bond-forming substituents of the flanking residues with respect to other functional groups and/or with respect to each other include pairs of differentially removable carboxy protective groups, such as a reduction-labile carboxy protective group, e.g. allyl or benzyl esters, paired with a base-labile carboxy protective group, e.g. fluorenylmethylesters, methyl or other primary alkyl esters. Fluorenylmethyl, methyl or other primary alkyl groups or other base-labile carboxy protective groups can be removed from their corresponding esters to yield a free carboxy group (without deprotecting allyl or benzyl esters or other reduction-labile esters) by saponification of the esters with a suitable base such as piperidine and sodium hydroxide in a suitable solvent such as dimethylacetamide, or methanol and water, for a period of 10 to 120 minutes, and preferably 20 minutes, 0° C. to 50° C. The allyl or benzyl or other reduction-labile esters can be removed when desired by reduction in the presence of a suitable transition metal catalyst, such as $Pd(PPh_3)_4$, $Pd(PPh_3)_2Cl_2$, $Pd(OAc)_2$ or Pd on carbon with a source of hydrogen, e.g. $H_2$ gas, in a suitable solvent such as dimethylacetamide, dimethylformamide, N-methylpyrrolidinone or methanol for a period of 10 to 500 minutes, and preferably 100 minutes, at 0° C. to 50° C. For the sake of simplicity and convenience, all carboxy protective groups that are removable by Pd-catalyzed methods which result in the reduction of the protected carboxy substitutent are included n the term "reduction-labile protective groups" as used herein, even though such Pd-catalyzed deprotection methods may not result in the reduction of the protective group in question.

In embodiments wherein Pd catalysis involves the formation of intermediates of Pd derivatized with reduction-labile protecting groups, e.g. Pd-allyl derivatives, the Pd catalyst can be restored by reaction with a suitable nucleophile, such as piperidine or tributyltin hydride. When such reduction-labile groups are used to provide orthogonal protection in combination with base-labile protecting groups, it is preferable to either (1) utilize a synthetic scheme that calls for the removal of the base-labile protecting groups before the removal of the reduction-labile protecting groups or (2) restore the Pd catalyst with a nucleophile that does not deprotect the base-labile protecting groups.

Alternatively, the carboxy substituents of the flanking residues can be orthogonally protected with respect the other functional groups and/or with respect to each other by using an acid-labile protecting group, such as a tertiary alkyl ester, e.g. t-butyl ester, in combination with a reduction-labile protecting group, such as the allyl or benzyl esters described above. The tertiary alkyl or other acid-labile ester group can be removed by acidolysis, e.g. with trifluoroacetic acid in methylene chloride, and the allyl or benzyl or other reduction-labile esters can be removed by reduction in the presence of a transition metal catalyst as described above.

In another embodiment, the carboxy substituents of the flanking residues can be orthogonally protected with respect to other functional groups and/or with respect to each other by using a fluoride ion-labile protecting group, such as 2-(trimethylsilyl)ethyl and silyl esters, in combination with a reduction-labile protecting group, such as the allyl or benzyl esters described above, or in combination with a base-labile protecting group, such as the fluorenylmethyl, methyl or other primary alkyl esters described above, without deprotecting the reduction-labile or base-labile esters. The 2-(trimethylsilyl)ethyl, silyl or other fluoride-labile ester group can be removed by reaction with a suitable fluoride ion source, such as tetrabutylammonium fluoride in the presence of a suitable solvent, such as dimethylacetamide (DMA), dimethylformamide (DMF), tetrahydrofuran (THF), or acetonitrile.

Suitable protecting groups for use in orthogonally protecting the side chain amide bond-forming substituents of the flanking residues with respect to other functional groups and/or with respect to each other also include pairs of differentially removable amino protective groups, such as an allyloxycarbonyl or other reduction-labile amino protective group paired with a t-butoxycarbonyl (Boc) or other acid-labile amino protective group, and a reduction-labile amino protective group paired with a fluorenylmethoxycarbonyl (Fmoc) or other base-labile amino protective group. An allyloxycarbonyl (or other reduction-labile blocking group) protected amino group can be deprotected by reduction using a transition metal catalyst as in the procedure for removing reduction-labile carboxy protective groups described above, without deprotecting a Boc or Fmoc protected amino group. Likewise, an acid-labile amino protective group and a base-labile amino protective group can be removed by acidolysis and base saponification, respectively, without removing a reduction-labile amino protective group. For the sake of simplicity and convenience, all amino protective groups that are removable by Pd-catalyzed methods which result in the reduction of the protected amino substitutent are included in the term "reduction-labile protective groups" as used herein, even though such Pd-catalyzed deprotection methods may not result in the reduction of the protective group in question.

In another embodiment, the amino substituents of the flanking residues can be orthogonally protected with respect to other functional groups and/or with respect to each other by using a fluoride-labile protecting group, such as 2-trimethylsilylethylcarbamate (Teoc), in combination with a reduction-labile protecting group, such as allyloxylcarbonyl, or in combination with a base-labile protecting group, such as fluorenylmethoxycarbonyl, as described above. The Teoc or other fluoride-labile group can be removed by reaction a with a suitable fluoride ion source, such as tetrabutylammonium fluoride, as in the procedures for removal of fluoride-labile carboxy protective groups described above, without deprotecting an allyloxycarbonyl or fluorenylmethoxycarbonyl protected amino group. Likewise, a reduction-labile amino protective group and a base-labile amino protective group can be removed by reduction and base saponification, respectively, without removing a fluoride-labile amino protective group.

In embodiments that use a carboxy substituent as the side chain amide bond-forming substituent of one flanking residue and that use an amino substituent as the side chain amide bond-forming substituent of the other flanking residue, the carboxy substituent and the amino substituent can be orthogonally protected with respect to each other by using a reduction-labile protecting group to block one substituent, e.g. allyl ester or allyloxycarbonyl, and a fluoride-labile, acid-labile or base-labile protecting group to block other substituent, e.g. silyl ester, t-butyl ester, fluorenylmethyl ester, Teoc, Boc, or Fmoc.

In a preferred embodiment, a reduction-labile protecting group is used to block the side chain amide bond-forming substituent of one flanking residue and the protecting group for the side chain amide bond-forming substituent of the other flanking residue is selected such that it provides orthogonal protection with respect to both the reduction-labile protecting group and the α-amino protecting group used in the synthesis. For example, in an embodiment using Fmoc chemistry for peptide synthesis, orthogonal protection of the side chain amide bond-forming substituents would be provided by a reduction-labile protecting group and an acid-labile protecting group. Likewise, in an embodiment using Boc chemistry for peptide synthesis, orthogonal protection of the side chain amide bond-forming substituents would be provided by a reduction-labile protecting group and a base-labile protecting group.

In yet another preferred embodiment, the side chain amide bond-forming substituents of the flanking residues are orthogonally protected with respect to each other, with respect to α-amino protecting group used in the synthesis, and with respect to the protecting groups used to block other side chain functional groups in the peptide chain.

In still another preferred embodiment, the side chain amide bond-forming substituents of the flanking residues are orthogonally protected with respect to each other, and with respect to α-amino protecting group, but only one of the side chain amide bond-forming substituents is orthogonally protected with respect to the protecting groups used to block other side chain functional groups. In this embodiment, it is preferable to use the side chain amide bond-forming substituent with fully orthogonal protection as the target for initial attachment of the compound to the difunctional linker. Since the side chain amide bond-forming substituent with fully orthogonal protection can be deprotected without deprotecting other functional groups, the amide bond-forming reaction will be specific to the desired side chain amide bond-forming substituent, and will reduce the production of unwanted difunctional linker derivatives. Although cyclization will require the deprotection of the side chain amide bond-forming substituent of the other flanking residue, and may cause concomitant deprotection of other side chain functional groups, unwanted derivatives are less likely to form given that the peptide chains are anchored to a solid support and that the linker length will regioselectively favor a amide bond-forming reaction between the unbound functional group of the linker and the side chain amide bond-forming substituent of the other flanking residue. If further peptide chain synthesis is desired after cyclization, any side chain functional groups on other amino acid residues left unprotected by the cyclization reactions can be reprotected before chain synthesis is resumed.

Many of the blocked amino acids described above can be obtained from commercial sources such as Novabiochem (San Diego, Calif.), Bachem Calif. (Torrence, Calif.) or Peninsula Labs (Belmont, Calif.). Alternatively, functionalized or protected amino acids, including unnatural amino acids, can be prepared by methods known in the art.

In addition, the compounds of the invention can be prepared by, or in conjunction with, solution phase peptide synthesis, for example, the solution phase peptide synthesis methods described in Principles of Peptide Synthesis, 2d ed, M. Bodanszky, Springer-Verlag (1993) or in The Practice of Peptide Synthesis, 2d ed, M. Bodanszky and A. Bodanszky, Springer-Verlag (1994). It will be appreciated that solution phase peptide synthesis methods can be easily modified to incorporate the desired flanking residues, with or without orthogonally-protected side chain amide bond-forming substituents, into the compound of interest, using procedures similar to those used in the solid phase synthesis methods described herein.

Administration of Compounds of the Invention

For clinical applications, compounds of the present invention may generally be administered, e.g., parenterally, intravenously, subcutaneously, intramuscularly, colonically, nasally, intraperitoneally, rectally, buccally, or orally, to a subject in need thereof. Compositions containing at least one compound of the invention that are suitable for use in human or veterinary medicine may be presented in forms permitting administration by a suitable route. These compositions may be prepared according to the customary methods, using one or more pharmaceutically acceptable adjuvants or excipients. The adjuvants comprise, inter alia, diluents, sterile aqueous media, and various non-toxic organic solvents. Acceptable carriers or diluents for therapeutic use are well known in the pharmaceutical field, and are described, for example, in *Remington: The Science and Practice of Pharmacy* (20th ed.), ed. A. R. Gennaro, Lippincott Williams & Wilkins, 2000, Philadelphia, and *Encyclopedia of Pharmaceutical Technology*, eds. J. Swarbrick and J. C. Boylan, 1988-1999, Marcel Dekker, New York. The compositions may be presented in the form of tablets, pills, granules, powders, aqueous solutions or suspensions, injectable solutions, elixirs, or syrups, and the compositions may optionally contain one or more agents chosen from the group comprising sweeteners, flavorings, colorings, and stabilizers in order to obtain pharmaceutically acceptable preparations.

The choice of vehicle and the content of active substance in the vehicle are generally determined in accordance with the solubility and chemical properties of the product, the particular mode of administration, and the provisions to be observed in pharmaceutical practice. For example, excipients such as lactose, sodium citrate, calcium carbonate, and dicalcium phosphate and disintegrating agents such as starch, alginic acids, and certain complex silicates combined with lubricants (e.g., magnesium stearate, sodium lauryl sulfate, and talc) may be used for preparing tablets. To prepare a capsule, it is advantageous to use lactose and high molecular weight polyethylene glycols. When aqueous suspensions are used, they may contain emulsifying agents which facilitate suspension. Diluents such as sucrose, ethanol, polyethylene glycol, propylene glycol, glycerol, chloroform, or mixtures thereof may also be used.

For parenteral administration, emulsions, suspensions, or solutions of the compositions of the invention in vegetable oil (e.g., sesame oil, groundnut oil, or olive oil), aqueous-organic solutions (e.g., water and propylene glycol), injectable organic esters (e.g., ethyl oleate), or sterile aqueous solutions of the pharmaceutically acceptable salts are used. The solutions of the salts of the compositions of the invention are especially useful for administration by intramuscular or subcutaneous injection. Aqueous solutions that include solutions of the salts in pure distilled water may be used for intravenous administration with the proviso that (i) their pH is adjusted suitably, (ii) they are appropriately buffered and rendered isotonic with a sufficient quantity of glucose or sodium chloride, and (iii) they are sterilized by heating, irradiation, or microfiltration. Suitable compositions containing the compounds of the invention may be dissolved or suspended in a suitable carrier for use in a nebulizer or a suspension or solution aerosol, or may be absorbed or adsorbed onto a suitable solid carrier for use in a dry powder inhaler. Solid compositions for rectal administration include suppositories formulated in accordance with known methods and containing at least one compound of formula I or II.

Dosage formulations of the compounds of this invention to be used for therapeutic administration must be sterile. Sterility is readily accomplished by filtration through sterile membranes (e.g., 0.2 micron membranes) or by other conventional methods. Formulations typically are stored in lyophilized form or as an aqueous solution. The pH of the compositions of this invention is typically between 3 and 11, more desirably between 5 and 9, and most desirably between 7 and 8, inclusive. While a desirable route of administration is by injection such as intravenously (bolus and/or infusion), other methods of administration may be used. For example, compositions may be administered subcutaneously, intramuscularly, colonically, rectally, nasally, or intraperitoneally in a variety of dosage forms such as suppositories, implanted pellets or small cylinders, aerosols, oral dosage formulations, and topical formulations such as ointments, drops, and dermal patches. Furthermore, the compounds of the invention may be coupled to a class of biodegradable polymers useful in achieving controlled release of a drug, for example polylactic acid, polyglycolic acid, copolymers of polylaclic and polyglycolic acid, polyepsilon caprolactone, polyhydroxy butyric acid, polyorthoesters, polyacetals, polydihydropyrans, polycyanoacrylates, and cross linked or amphipathic block copolymers of hydrogels.

The compounds of the invention may also be administered in the form of liposome delivery systems, such as small unilamellar vesicles, large unilamellar vesicles, and multilamellar vesicles. Liposomes can be formed from a variety of lipids, such as cholesterol, stearylamine, or phosphatidylcholines. The compounds of the invention may also be delivered using antibodies, antibody fragments, growth factors, hormones, or other targeting moieties to which the compound molecules are coupled (e.g., see *Remington: The Science and Practice of Pharmacy*, vide supra).

In the case of use of nucleic acids such as vectors adapted to express a compound of the invention or, for example, adapted to produce antisense, ribozymes, or iRNA in use, or also in the case of antisense molecules, ribozymes or siRNA themselves, suitable carriers include water, aqueous saline solution, aqueous dextrose solution, and the like, with isotonic solutions being preferred for intravenous administration. As is mentioned elsewhere herein, the nucleic acid vectors of the invention may also be formulated into vehicles such as liposomes, which are especially suitable for administration of the nucleic acid vectors to tissues and tumours, or into biodegradable polymers such as poly(lactic acid), poly (lactide-co-glycolide) (PLGA), atelocollagen, or other polymers as non-viral gene delivery systems. In a particularly preferred form of the invention, nucleic acid vectors are packaged into suitable viral particles, as mentioned hereinbefore.

Dosage levels of active ingredients in the pharmaceutical compositions of the invention may be varied to obtain an amount of the active compound(s) that achieves the desired therapeutic response for a particular patient, composition, and mode of administration. The selected dosage level depends upon the activity of the particular compound, the route of administration, the severity of the condition being treated, and the condition and prior medical history of the patient being treated. For adults, the doses are generally from about 0.01 to about 100 mg/kg, desirably about 0.1 to about 1 mg/kg body weight per day by inhalation, from about 0.01 to about 100 mg/kg, desirably 0.1 to 70 mg/kg, more desirably 0.5 to 10 mg/kg body weight per day by oral administration, and from about 0.01 to about 50 mg/kg, desirably 0.1 to 1 mg/kg body weight per day by intravenous administration. Doses are determined for each particular case using standard methods in accordance with factors unique to the patient, including age, weight, general state of health, and other factors which can influence the efficacy of the compound(s) of the invention.

Administration of compositions of the invention may be as frequent as necessary to obtain the desired therapeutic effect. Some patients may respond rapidly to a higher or lower dose and may find much weaker maintenance doses adequate. Other patients, however, receive long-term treatments at the rate of 1 to 4 doses per day, in accordance with the physiological requirements of each patient. The active product may be administered, e.g., intravenously, 1 to 4 times daily or via continuous infusion.

The following non-limiting examples are provided to further describe various aspects and embodiments of the present invention.

Methods Used in the Examples

Construction of GST-DT (140-271):

APCR based cloning technique was used for the construction of glutathione-S-transferase diphtheria toxin 140-271 fusion protein. The oligonucleotide primers used to amplify diphtheria tox gene sequences encoding amino acids 140 to 271 were as follows:

```
5'-CGCGGATCCCCCTTCGCTGAGGGGAGT-3'

3'-CCGCTCGAGCGGGTTGGTACCAGTAAC-5'
```

The oligonucleotide sequences also introduced BamHI and XhoI restriction endonuclease sites on the 5'- and 3'-ends of the amplicon, respectively. In this construct, the translation termination signal is encoded by the vector following the addition of LeuGluArgProHisArgAsp to the C-terminal end of DT140-271 sequences.

Following amplification and digestion with BamHI and XhoI, the doubled stranded DNA was cloned into the corresponding sites in pGEX-4T-1, to form pGEX-DT-T1. Following transformation of *E. coli*, and selection of a single clone, the DNA sequence of the insert was determined to ensure maintenance of the correct reading frame through the fusion junction.

Figure 4:
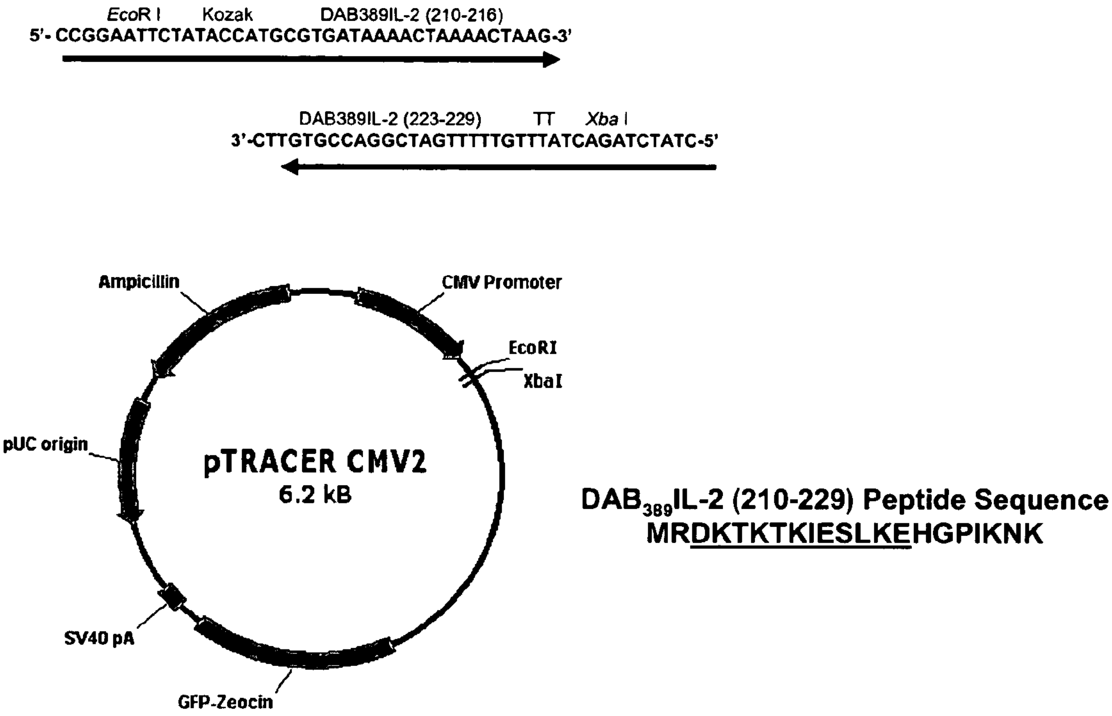
FIG. 4 is a schematic showing the pTRACER-CMV2 expression vector and the oligonucleotide primers used in PCR amplification of amino acids 210-229 from $DAB_{389}$IL-2.

Construction of pTRACER-T1 and pRR-XT1 Vectors:

The pTRACER-CMV2 expression vector was obtained from Invitrogen. The oligonucleotide primers used for the PCR amplification of amino acids 210-229 from $DAB_{389}$IL-2 are shown in FIG. 4. The oligonucleotide encoding the 5'-end of the construct was modified to include an EcoR1 restriction endonuclease site, a Kozak signal (Kozak, 1991), and an ATG translation initiation signal. The oligonucleotide encoding the 3'-end of the sequence included a translation termination signal (TT) and an Xba1 site. Following PCR amplification, the oligonucleotides were annealed, digested with EcoR1 and Xba1 and ligated into the EcoR1 and Xba1 sites of the pTRACER-CMV2 vector. The predicted amino acid sequence for the "translocation motif" peptide, T1, is shown.

The pRR-XT1 vector was constructed from the psiRNA-hH1neo vector (Invivogen) by ligating the SirF/SirR double stranded oligonucleotides into the BglI restriction endonuclease site. The SirF oligonucleotide (5'-TCCCACACTAAGATCGAATCTCTGATCAAGAGATCAGAGATTCGATCTTA-3') was annealed to the SirR oligonucleotide (3'-ATTCTAGCTTAGAGACTAGTTCTCTAGTCTCTAAGCTAGAATCAAAAAC-5') under standard conditions. Following hybridization and ligation into the BglI site of psiRNA-hHneo vector, *E. coli* 6T116 was transformed, single colonies were isolated, and their plasmid DNA sequenced to insure insertion of the siRNA encoding oligonucleotides. The hairpin siRNA expressed from pRR-XT1 is predicted to have the following structure:

```
                    C
                 U     A
UAAGAUCGAAUCUCUGA
                          A
                          G
AUUCUAGCUUAGAGACU
                 A     A
                    G
```

PCR Detection of mRNA Transcripts Encoding the "Translocation Motif" Peptide:

Total RNA was extracted from Hut102/6TG and Hut102/6TG-T1 cells according to standard methods. Oligonucleotide primers used for detection of "translocation motif" mRNA are as follows: Forward T1 primer: 5'-CCATGAGTGATAAAACTAAA-3'; Reverse T1 primer: 5'-ATTAGGAAAGGACAGTGGGA-3'.

In Gel Digestion of Protein:

Following SDS-polyacrylamide gele electrophoresis, proteins were digested in situ with trypsin was performed as described (Rosenfeld et al., 1992; Wilm and Mann, 1996). In brief, individual protein bands in the SDS-polyacrylamide gele were cut into small pieces and dehydrated with acetonitrile. The contents were re-hydrated with 10 mM DTT in 100 mM ammonium bicarbonate and incubated at 56° C. for one hour. The gel pieces were then treated with 10 mM iodoacetamide in 100 mM ammonium bicarbonate. Following dehydration with acetonitrile, gel pieces were suspended in trypsin (12.5 ng/μl) in 50 mM ammonium bicarbonate. In gel digestion was carried out at 37° C. for 10-12 hours. The peptides were extracted in 50% acetonitrile/5% formic acid.

Protein Identification by Mass Spectrometry Sequencing:

Tryptic peptides were analyzed by MALDI-TOF-MS (Voyager DE-PRO, ABI, Framingham, Mass.) and electrospray ionization mass spectrometry (ESI-MS). ESI-MS and MS/MS were performed using an electrospray iontrap, LCQ-DECA (Thermo Electron, CA). The tryptic peptides were fractionated on capillary HPLC C-18 column coupled with mass spectrometer. Tandem mass spectra were acquired using Ar as the collision gas and sufficient collision energy to obtain complete sequence information of the precursor ion. MS and MS/MS data was then analyzed by BioWorks 3.0 software package (Thermo Electron, CA).

Cytotoxicity Assays:

Cytotoxicity assays were performed essentially as described by vanderSpek et al., *J. Biol. Chem.* 269(34):21455-9, 1994. Hut102/6TG cells were maintained in RPMI 1640 medium supplemented with 10% fetal bovine serum, 2 mM L-glutamine, 50 IU/ml penicillin, and 50 μg/ml streptomycin. Cells were seeded at $5\times10^4$ cells in 100 μl of complete medium per well in 96 well plates. The fusion protein toxins were diluted in complete medium such that addition of 100 μl volumes resulted in final concentrations of the toxin ranging from $10^{-7}$ to $10^{-12}$ M. The plates were incubated for 18 hrs at 37° C. in a 5% $CO_2$ atmosphere and then centrifuged at 170×g for 5 min. The medium was aspirated carefully and replaced with 200 μl leucine-free minimal essential medium containing 1.0 μCi/ml [$^{14}$C]-leucine, 2 mM L-glutamine, 50 IU/ml penicillin, and 50 μg/ml streptomycin. The cell cultures were then incubated for 90 min at 37° C. in a 5% $CO_2$ atmosphere. The cells were pelleted as before, the medium carefully removed, and then lysed by the addition of 60 μl/well of 0.4 M KOH. Total protein was then precipitated by the addition of 140 μl 10% trichloroacetic acid. The precipitate was collected on Whatman GF/A glass fiber filters using a PhD cell harvester. Radioactivity was determined according to standard conditions. Medium alone served as the control and assays were performed in quadruplicate.

Synthesis of T1 and Control Peptides:

A synthetic 'transmembrane motif' peptide with the sequence RDKTKTKIESLKEHGPIKNS (the T1 peptide of SEQ ID NO 2) was prepared by solid-phase peptide synthesis and purified to 91.3% by high performance liquid chromatography by 21$^{st}$ Century Biochemicals, Inc., Marlboro, Mass. The T1 peptide has a molecular weight of 2,351 and a pI of 9.8. A 2,335 molecular weight peptide with the sequence AENSDKHRIMQVFHRTLNQ and pI of 8.8 was used as a negative control in GST-DT140-271 pull down experiments.

EXAMPLES

Example 1

In Vitro Translocation Assay Analyzed by Electrophoresis

Cells were lysed and early endosomes were partially purified by sucrose density centrifugation as previously described (Lemichez et al., *Mol. Microbiol.* 23:445, 1997; Ratts et al., *J. Cell Biol.* 160:1139, 2003). In vitro translocation assays were performed in 25 μL mixtures containing 4 μL purified early endosomes in translocation buffer (50 mM Tris-HCl, pH 7.4, 25 mM EDTA). ATP and Hut102/6TG cytosol were added to 2 mM and 0.09 μg/mL, respectively, and mixture was incubated at 37° C. for 30 min. Following incubation the translocation mixture was ultracentrifuged at 180,000×g at 4° C. to separate the supernatant fluid (translocated and released C-domain) from the pellet fraction (non-translocated C-domain). The pellet fraction was then lysed by the addition of 0.2% Triton X-100.

The in vitro $NAD^+$ dependent ADP-ribosylation of EF-2 was performed according to a procedure modified from Chung et al., *Biochim. Biophys. Acta.* 483:248-57, 1977. Briefly, the reaction mixture contained 20 mM HEPES-KOH, pH 7.4, 1 mM $Mg(OAc)_2$, 110 mM KOac, 1 mM DTT, 0.13 mg/mL purified elongation factor 2 (EF-2), 1.2 pmol [$^{32}$P]-$NAD^+$ (Perkin Elmer), and either translocation mixture supernatant fluid or pellet fractions. The ADP-ribosyltransferase reaction was initiated by the addition of [$^{32}$P]-$NAD^+$, and stopped by the addition of SDS-polyacrylamide gel electrophoresis sample buffer (125 mM Tris-HCl, pH 6.8, 20% glycerol, 0.005% bromophenol blue, 10% β-mercaptoethanol, and 4% sodium dodecylsulfate). Reaction mixtures were analyzed by electrophoresis on 7% SDS-polyacrylamide gels at 150 V for 2.1 hrs. Gels were then dried and autoradiographed. As shown in FIG. 1A, approximately 60% of the ADP-ribosyltransferase activity from $DAB_{389}$IL-2 is translocated from the endosomal lumen to the external medium in the 30 min incubation period. In marked contrast, essentially all of the ADP-ribosyltransferase activity from $DAB_{389}$(L221E)IL-2 remains in the pellet fraction. This result demonstrates that the non-toxic phenotype of the L221E mutant is a result of a defect in C-domain translocation and release into the cytosol of cells.

Example 2

In Vitro Translocation Assay Analyzed by Fluorescence Analysis

In another in vitro assay, the translocation of the diphtheria toxin C-domain from the lumen of purified early endosomes was performed as described by Ratts et al. (*J. Cell Biol.* 160:1139, 2003). Early endosomes were isolated from Hut102/6TG cells as described by Duprez and Dautry-Versat (*J. Biol. Chem.* 261(33): 15450-4, 1986). Prior to isolation, the endosomal compartment was pre-loaded with either 1 μM $DAB_{389}$IL-2 or $DAB_{389}$(L221E)IL-2, and/or 8 mg/mL 70-kD OG514-dextran conjugate (Molecular Probes) using 1 μM bafilomycin A1-primed cells (Sigma-Aldrich).

Following cell lysis and partial purification of the early endosome fraction by sucrose density gradient centrifugation, endosomes pre-loaded with OG514 dextran conjugate alone were resuspended in translocation buffer in the absence (▲) or presence (○) of 2 mM ATP. Endosomes that were pre-loaded with either OG514 conjugate and $DAB_{389}$L-2 (■, wild type) or OG514 conjugate and $DAB_{389}$(L221E)IL-2 (◇, mutant) were resuspended in translocation buffer in the presence of 2 mM ATP. Fluorescence Emission was measured at an excitation wavelength of 511 nm and an emission wavelength of 530 nm. Values were compared to 1 ng/mL OG 514 conjugate standards at pH 7.5 and 4.5.

The results, shown in FIG. 1B, indicate that both the wild type and mutant fusion protein toxins are capable of forming ion-conductive channels in the endosomal vesicle membrane. These results also suggest that the non-cytotoxic phenotype of $DAB_{389}$(L221E)IL-2 is due to a specific defect in C-domain translocation and release into the cytosol of cells.

Example 3

Dose Response Analysis of Hut102/6TG, Hut102/6TG-T1, and Hut102/6TG-T1/pRR-XT1 Cells to $DAB_{389}$IL-2

Individual cell lines of Hut102/6TG, Hut102/6TG-T1, and Hut102/6TG-T1/pRR-XT1 cells were seeded at $5\times10^4$ cells per well in 96 well plates and incubated in the absence of presence of varying concentrations of $DAB_{389}$IL-2 for 18 hrs at 37° C. in 5% $CO_2$. The cells were then washed and resuspended in minimal (leucine depleted) medium containing [$^{14}$C]-leucine and pulse labeled for 2 hrs at 37° C. in 5% $CO_2$.

The cells were then lysed with 0.4M KOH, incubated for 10 min, and total protein was precipitated by the addition of 10% trichloroacetic acid (TCA). Protein precipitates were collected on glass fiber filters (Whatman GF/A) using a PhD cell harvester and radioactivity was measured according to standard methods. Cells incubated in medium alone served as controls. The results from three separate experiments in which each fusion protein toxin concentration was assayed in quadruplicate are presented in FIG. 2. Results [Hut102/6TG (●), Hut102/6TG-T1 (■), and Hut102/6TG-T1/pRR-XT1 (▲)] are presented as percent control level of [$^{14}$C]-leucine incorporation. The $IC_{50}$ for $DAB_{389}$IL-2 in Hut102/6TG cells was found to be $5\times10^{-11}$M. In marked contrast, the $IC_{50}$ for $DAB_{389}$IL-2 in Hut102/6TG-T1 cells was greater than $10^{-8}$M. The results showed that cells having cytosolic T1 peptide conjugate were resistant to diphtheria toxin intoxication as a result of CTF inhibition, resulting in loss of C-domain translocation Example 4

Hut102/6TG Cell Lysate Preparation and GST-pull Down

GST and the fusion protein GST-DT(140-271) were expressed in *E. coli* strain BL-21(DE-3) transformed with either pGEX-T4-1 or pGEX-DT-T1 and purified as described (Bharti et al., *J. Biol. Chem.* 271(4):1993-7, 1996). Purified GST and GST-DT(140-271) were eluted from glutathione sepharose beads by elution buffer (10 mM reduced glutathione, 150 mM NaCl, 50 mM Tris HCl, pH 8.0). The eluted protein was dialyzed against PBS for twelve hours at 4° C. Protein concentrations were determined by the modified Bradford reagent (BioRad). Following purification, GST and GST-DT(140-271) were separately incubated with glutathione sepharose beads (1 ml GS beads per mg recombinant protein) at 4° C. for two hours in PBS. The resulting GST and GST-DT(140-271) beads were then used in pull down experiments.

Hut102/6TG cells were resuspended in hypotonic buffer (10 mM Tris HCl, pH 7.3, 10 mM KCl, 1.5 mM $MgCl_2$, 1 mM EDTA and 1 mM DTT) and incubated at 4° C. for 30 min. The cells were homogenized and the resulting lysate was centrifuged at 100,000×g for 1 hour and then dialyzed with buffer A (30 mM Tris HCl, pH 7.4, 5 mM $MgCl_2$, 1 mM EDTA and 1 mM DTT). Equal volumes of dialyzed cytoplasmic lysate were separately passed through GST and GST-DT columns. This step was repeated three times to provide sufficient time for proteins in the extract to bind to GST and GST-DT(140-271). The columns were then washed with ten column volumes of buffer A. After the final wash, 1 ml of buffer B (buffer A+150 mM NaCl) was used to elute interacting proteins. The eluted proteins were collected in five fractions of 200 μL. Additional proteins bound to the columns were eluted and fractionated with 1 ml of buffer C (buffer A+500 mM NaCl). The fractions containing interacting proteins were then analyzed by electrophoresis on SDS-PAGE gels followed by silver staining, as shown in FIG. 3A.

Hut102/6TG cells were resuspended in lysis buffer (150 mM NaCl, 50 mM Tris HCl, pH 7.4, 1% NP-40, 1 mM DTT, 1 mM sodium vanadate, and a cocktail of protease inhibitors with EDTA). Cells were incubated at 4° C. for 30 min and centrifuged at 13,000×g for 15 min. The supernatant fluid fraction was used in peptide competition assays as follows. Twenty μg recombinant GST and GST-DT140-271 proteins were incubated with 650 μg of Hut102/6TG cell lysate in the presence of increasing concentration (1.25, 2.5, 5 and 10 μM) of T1 peptide. A peptide with similar molecular mass and pI was also used as the negative control. Analysis of the protein interactions were again performed by electrophoresis on SDS-PAGE gels followed by silver staining. The results are presented in FIG. 3B. These results demonstrate that, like Hsp 90 and thioredoxin reductase, β-COP plays a direct role in C-domain translocation from the lumen of early endosomes and serves as an essential component of the cytosolic translocation factor (CTF) complex.

SEQ ID NO. 1 (consensus peptide sequence of CTF-binding moiety)
RDKTKTKIESLKEHGPIKNS SEQ ID NO. 2 (T1 peptide)
TQIENLKEKG All publications and patents cited in this specification are hereby incorporated by reference herein as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying a compound that is capable of inhibiting cell death in a mammal comprising the following steps:

a) isolating, from a mammalian cell, an early endosome comprising a toxin selected from the group consisting of Diptheria toxin, Botulinum toxin, Anthrax toxin Lethal Factor (LF), and Anthrax toxin Edema Factor (EF);

b) placing said endosomes in a cytosolic buffer;

c) contacting said endosomes with a cytosolic translocation factor complex, comprising beta-COP;

d) contacting said endosomes with said compound;

e) acidifying said endosome; and f) measuring translocation of said toxin, wherein a decreased level of said translocation relative to that observed in the absence of said compound indicates that said compound is capable of inhibiting said cell death.

2. The method of claim 1, wherein said toxin is a fusion protein comprising IL-2.

3. The method of claim 2, wherein said toxin is $DAB_{389}$IL-2.

4. The method of claim 1, wherein said cytosolic translocation factor comprises Hsp 90.

5. The method of claim 1 wherein said cytosolic translocation factor comprises TrR-1.

6. The method of claim 1, wherein measuring said translocation comprises measuring the ADP-ribosylation of elongation factor-2.

7. The method of claim 1, wherein said toxin Diphtheria toxin.

8. A method of identifying a compound that is capable of promoting cell death in a mammal comprising the following steps:

a) isolating, from a mammalian cell, an early endosome comprising a toxin selected from the group consisting of Diptheria toxin, Botulinum toxin, Anthrax toxin Lethal Factor (LF), and Anthrax toxin Edema Factor (EF);

b) placing said endosomes in a cytosolic buffer;

c) contacting said endosomes with a cytosolic translocation factor complex, comprising beta-COP;

d) contacting said endosomes with said compound;

e) acidifying said endosome; and f) measuring translocation of said toxin, wherein a decreased level of said translocation relative to that observed in the absence of said compound indicates that said compound is capable of promoting said cell death.

9. The method of claim 8, wherein said toxin is a fusion protein comprising IL-2.

10. The method of claim 9, wherein said fusion protein is $DAB_{389}$IL-2.

11. The method of claim 8, wherein said cytosolic translocation factor comprises Hsp 90.

12. The method of claim 8, wherein said cytosolic translocation factor comprises TrR-1.

13. The method of claim 8, wherein measuring said translocation comprises measuring the ADP-ribosylation of elongation factor-2.

14. The method of claim 8, wherein said toxin is Diphtheria toxin.

15. The method of claim 8, wherein said toxin is Botulinum toxin.

16. The method of claim 8, wherein said toxin is Anthrax toxin Lethal Factor (LF).

17. The method of claim 8, wherein said toxin is Anthrax toxin Edema Factor (EF).

18. The method of claim 8, wherein said mammalian cell is a human cell.

19. The method of claim 1, wherein said toxin is Botulinum toxin.

20. The method of claim 1, wherein said toxin is Anthrax toxin Lethal Factor (LF).

21. The method of claim 1, wherein said toxin is Anthrax toxin Edema Factor (EF).

22. The method of claim 1, wherein said mammalian cell is a human cell.

* * * * *

SEQUENCE LISTING

```
<160> NUMBER OF SEQ ID NOS: 6

<210> SEQ ID NO 1
<211> LENGTH: 6249
<212> TYPE: DNA
<213> ORGANISM: Artificial Sequence
<220> FEATURE:
<223> OTHER INFORMATION: Plasmid pP1

<400> SEQUENCE: 1

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccactagt ccagtgtggt ggaattctat    960

accatgcgtg ataaaactaa aactaagatc gaatctctga aagaacacgg tccgatcaaa   1020

aacaaatagt ctagagggcc cgtttaaacc cgctgatcag cctcgactgt gccttctagt   1080

tgccagccat ctgttgtttg cccctccccc gtgccttcct tgaccctgga aggtgccact   1140

cccactgtcc tttcctaata aaatgaggaa attgcatcgc attgtctgag taggtgtcat   1200

tctattctgg ggggtggggt ggggcaggac agcaaggggg aggattggga agacaatagc   1260

agctttgcaa agatggataa agttttaaac agagaggaat ctttgcagct aatggacctt   1320

ctaggtcttg aaaggagtgc ctcgtgaggc tccggtgccc gtcagtgggc agagcgcaca   1380

tcgcccacag tccccgagaa gttgggggga ggggtcggca attgaaccgg tgcctagaga   1440

aggtggcgcg gggtaaactg ggaaagtgat gtcgtgtact ggctccgcct ttttcccgag   1500

ggtgggggag aaccgtatat aagtgcagta gtcgccgtga acgttctttt tcgcaacggg   1560
```

-continued

```
tttgccgcca gaacacaggt aagtgccgtg tgtggttccc gcgggcctgg cctctttacg   1620
ggttatggcc cttgcgtgcc ttgaattact tccacctggc tgcagtacgt gattcttgat   1680
cccgagcttc gggttggaag tgggtgggag agttcgaggc cttgcgctta aggagcccct   1740
tcgcctcgtg cttgagttga ggcctggcct gggcgctggg gccgccgcgt gcgaatctgg   1800
tggcaccttc gcgcctgtct cgctgctttc gataagtctc tagccattta aaatttttga   1860
tgacctgctg cgacgctttt tttctggcaa gatagtcttg taaatgcggg ccaagatctg   1920
cacactggta tttcggtttt tggggccgcg ggcggcgacg gggcccgtgc gtcccagcgc   1980
acatgttcgg cgaggcgggg cctgcgagcg cggccaccga gaatcggacg ggggtagtct   2040
caagctggcc ggcctgctct ggtgcctggc ctcgcgccgc cgtgtatcgc cccgccctgg   2100
gcggcaaggc tggcccggtc ggcaccagtt gcgtgagcgg aaagatggcc gcttcccggc   2160
cctgctgcag ggagctcaaa atggaggacg cggcgctcgg gagagcgggc gggtgagtca   2220
cccacacaaa ggaaaagggc ctttccgtcc tcagccgtcg cttcatgtga ctccacggag   2280
taccgggcgc cgtccaggca cctcgattag ttctcgagct tttggagtac gtcgtcttta   2340
ggttgggggg aggggtttta tgcgatggag tttccccaca ctgagtgggt ggagactgaa   2400
gttaggccag cttggcactt gatgtaattc tccttggaat ttgccctttt tgagtttgga   2460
tcttggttca ttctcaagcc tcagacagtg gttcaaagtt tttttcttcc atttcaggtg   2520
tcgtgaggaa ttagcttggt actaatacga ctcactatag ggagacccaa gctggctagg   2580
taagctccta ggcttttgca aaaagctccc gggagcttgt atatccattt tcggatctga   2640
tcagcacgtg ttgacaatta atcatcggca tagtatatcg gcatagtata atacgacaag   2700
gtgaggaact aaaccatggc tagcaaagga gaagaacttt tcactggagt tgtcccaatt   2760
cttgttgaat tagatggtga tgttaatggg cacaaatttt ctgtcagtgg agagggtgaa   2820
ggtgatgcta catacggaaa gcttaccctt aaatttattt gcactactgg aaaactacct   2880
gttccatggc caacacttgt cactactttc tcttatggtg ttcaatgctt ttcccgttat   2940
ccggatcata tgaaacggca tgactttttc aagagtgcca tgcccgaagg ttatgtacag   3000
gaacgcacta tatctttcaa agatgacggg aactacaaga cgcgtgctga agtcaagttt   3060
gaaggtgata cccttgttaa tcgtatcgag ttaaaaggta ttgattttaa agaagatgga   3120
aacattctcg gacacaaact cgagtacaac tataactcac acaatgtata catcacggca   3180
gacaaacaaa agaatggaat caaagctaac ttcaaaattc gccacaacat tgaagatgga   3240
tccgttcaac tagcagacca ttatcaacaa aatactccaa ttggcgatgg ccctgtcctt   3300
ttaccagaca accattacct gtcgacacaa tctgcccttt cgaaagatcc caacgaaaag   3360
cgtgaccaca tggtccttct tgagtttgta actgctgctg ggattacaca tggcatggat   3420
gccaagttga ccagtgccgt tccggtgctc accgcgcgcg acgtcgccgg agcggtcgag   3480
ttctggaccg accggctcgg gttctcccgg gacttcgtgg aggacgactt cgccggtgtg   3540
gtccgggacg acgtgaccct gttcatcagc gcggtccagg accaggtggt gccggacaac   3600
accctggcct gggtgtgggt gcgcggcctg gacgagctgt acgccgagtg gtcggaggtc   3660
gtgtccacga acttccggga cgcctccggg ccggccatga ccgagatcgg cgagcagccg   3720
tgggggcggg agttcgccct gcgcgacccg gccggcaact gcgtgcactt cgtggccgag   3780
gagcaggact gacacgtgct acgagatttc gattccaccg ccgccttcta tgaaaggttg   3840
ggcttcggaa tcgttttccg ggacgccggc tggatgatcc tccagcgcgg ggatctcatg   3900
ctggagttct tcgcccaccc caacttgttt attgcagctt ataatggtta caaataaagc   3960
```

-continued

```
aatagcatca caaatttcac aaataaagca ttttttcac tgcattctag ttgtggtttg   4020
tccaaactca tcaatgtatc ttatcatgtc tgtataccgt cgacctctag ctagagcttg   4080
gcgtaatcat ggtcatagct gtttcctgtg tgaaattgtt atccgctcac aattccacac   4140
aacatacgag ccggaagcat aaagtgtaaa gcctggggtg cctaatgagt gagctaactc   4200
acattaattg cgttgcgctc actgcccgct ttccagtcgg gaaacctgtc gtgccagctg   4260
cattaatgaa tcggccaacg cgcggggaga ggcggtttgc gtattgggcg ctcttccgct   4320
tcctcgctca ctgactcgct gcgctcggtc gttcggctgc ggcgagcggt atcagctcac   4380
tcaaaggcgg taatacggtt atccacagaa tcaggggata acgcaggaaa gaacatgtga   4440
gcaaaaggcc agcaaaaggc caggaaccgt aaaaaggccg cgttgctggc gtttttccat   4500
aggctccgcc cccctgacga gcatcacaaa aatcgacgct caagtcagag gtggcgaaac   4560
ccgacaggac tataaagata ccaggcgttt ccccctggaa gctccctcgt gcgctctcct   4620
gttccgaccc tgccgcttac cggatacctg tccgcctttc tcccttcggg aagcgtggcg   4680
ctttctcaat gctcacgctg taggtatctc agttcggtgt aggtcgttcg ctccaagctg   4740
ggctgtgtgc acgaaccccc cgttcagccc gaccgctgcg ccttatccgg taactatcgt   4800
cttgagtcca acccggtaag acacgactta tcgccactgg cagcagccac tggtaacagg   4860
attagcagag cgaggtatgt aggcggtgct acagagttct tgaagtggtg gcctaactac   4920
ggctacacta gaaggacagt atttggtatc tgcgctctgc tgaagccagt taccttcgga   4980
aaaagagttg gtagctcttg atccggcaaa caaaccaccg ctggtagcgg tggttttttt   5040
gtttgcaagc agcagattac gcgcagaaaa aaaggatctc aagaagatcc tttgatcttt   5100
tctacggggt ctgacgctca gtggaacgaa aactcacgtt aagggatttt ggtcatgaga   5160
ttatcaaaaa ggatcttcac ctagatcctt ttaaattaaa aatgaagttt taaatcaatc   5220
taaagtatat atgagtaaac ttggtctgac agttaccaat gcttaatcag tgaggcacct   5280
atctcagcga tctgtctatt tcgttcatcc atagttgcct gactccccgt cgtgtagata   5340
actacgatac gggagggctt accatctggc cccagtgctg caatgatacc gcgagaccca   5400
cgctcaccgg ctccagattt atcagcaata aaccagccag ccggaagggc cgagcgcaga   5460
agtggtcctg caactttatc cgcctccatc cagtctatta attgttgccg ggaagctaga   5520
gtaagtagtt cgccagttaa tagtttgcgc aacgttgttg ccattgctac aggcatcgtg   5580
gtgtcacgct cgtcgtttgg tatggcttca ttcagctccg gttcccaacg atcaaggcga   5640
gttacatgat cccccatgtt gtgcaaaaaa gcggttagct ccttcggtcc tccgatcgtt   5700
gtcagaagta agttggccgc agtgttatca ctcatggtta tggcagcact gcataattct   5760
cttactgtca tgccatccgt aagatgcttt tctgtgactg gtgagtactc aaccaagtca   5820
ttctgagaat agtgtatgcg gcgaccgagt tgctcttgcc cggcgtcaat acgggataat   5880
accgcgccac atagcagaac tttaaaagtg ctcatcattg gaaaacgttc ttcggggcga   5940
aaactctcaa ggatcttacc gctgttgaga tccagttcga tgtaacccac tcgtgcaccc   6000
aactgatctt cagcatcttt tactttcacc agcgtttctg ggtgagcaaa aacaggaagg   6060
caaaatgccg caaaaaaggg aataagggcg acacggaaat gttgaatact catactcttc   6120
ctttttcaat attattgaag catttatcag ggttattgtc tcatgagcgg atacatattt   6180
gaatgtattt agaaaaataa acaaataggg gttccgcgca catttccccg aaaagtgcca   6240
cctgacgtc                                                          6249
```

-continued

```
<210> SEQ ID NO 2
<211> LENGTH: 270
<212> TYPE: DNA
<213> ORGANISM: Corynebacterium diphtheriae
<220> FEATURE:
<221> NAME/KEY: CDS
<222> LOCATION: (1)...(270)

<400> SEQUENCE: 2

agg gat aaa act aag aca aag ata gag tct ttg aaa gag cat ggc cct       48
Arg Asp Lys Thr Lys Thr Lys Ile Glu Ser Leu Lys Glu His Gly Pro
 1               5                  10                  15

atc aaa aat aaa atg agc gaa agt ccc aat aaa aca gta tct gag gaa       96
Ile Lys Asn Lys Met Ser Glu Ser Pro Asn Lys Thr Val Ser Glu Glu
            20                  25                  30

aaa gct aaa caa tac cta gaa gaa ttt cat caa acg gca tta gag cat      144
Lys Ala Lys Gln Tyr Leu Glu Glu Phe His Gln Thr Ala Leu Glu His
        35                  40                  45

cct gaa ttg tca gaa ctt aaa acc gtt act ggg acc aat cct gta ttc      192
Pro Glu Leu Ser Glu Leu Lys Thr Val Thr Gly Thr Asn Pro Val Phe
     50                  55                  60

gct ggg gct aac tat gcg gcg tgg gca gta aac ggt gcg caa gtt atc      240
Ala Gly Ala Asn Tyr Ala Ala Trp Ala Val Asn Gly Ala Gln Val Ile
 65                  70                  75                  80

gat agc gaa aca gct gat aat ttg gaa aag                              270
Asp Ser Glu Thr Ala Asp Asn Leu Glu Lys
                 85                  90


<210> SEQ ID NO 3
<211> LENGTH: 90
<212> TYPE: PRT
<213> ORGANISM: Corynebacterium diphtheriae

<400> SEQUENCE: 3

Arg Asp Lys Thr Lys Thr Lys Ile Glu Ser Leu Lys Glu His Gly Pro
 1               5                  10                  15

Ile Lys Asn Lys Met Ser Glu Ser Pro Asn Lys Thr Val Ser Gln Glu
            20                  25                  30

Lys Ala Lys Gln Tyr Leu Glu Glu Phe His Gln Thr Ala Leu Glu His
        35                  40                  45

Pro Gln Leu Ser Glu Leu Lys Thr Val Thr Gly Thr Asn Pro Leu Phe
    50                  55                  60

Ala Gly Ala Asn Tyr Ala Ala Trp Ala Val Asn Val Ala Gln Val Ile
65                  70                  75                  80

Asp Ser Glu Thr Ala Asp Asn Leu Glu Lys
                85                  90


<210> SEQ ID NO 4
<211> LENGTH: 13
<212> TYPE: PRT
<213> ORGANISM: Corynebacterium diphtheriae

<400> SEQUENCE: 4

Arg Asp Lys Thr Lys Thr Lys Ile Glu Ser Leu Lys Glu
 1               5                  10


<210> SEQ ID NO 5
<211> LENGTH: 20
<212> TYPE: PRT
<213> ORGANISM: Corynebacterium diphtheriae

<400> SEQUENCE: 5
```

-continued

```
Arg Asp Lys Thr Lys Thr Lys Ile Glu Ser Leu Lys Glu His Gly Pro
 1              5                   10                  15

Ile Lys Asn Lys
            20


<210> SEQ ID NO 6
<211> LENGTH: 19
<212> TYPE: PRT
<213> ORGANISM: Corynebacterium diphtheriae

<400> SEQUENCE: 6

Asp Trp Val Ile Arg Asp Lys Thr Lys Thr Lys Ile Glu Ser Leu Lys
 1              5                   10                  15

Glu His Gly
```